(12) United States Patent
Karni et al.

(10) Patent No.: US 11,103,479 B2
(45) Date of Patent: Aug. 31, 2021

(54) SMALL ORGANIC MOLECULES FOR USE IN THE TREATMENT OF NEUROINFLAMMATORY DISORDERS

(71) Applicant: THE MEDICAL RESEARCH, INFRASTRUCTURE AND HEALTH SERVICES FUND OF THE TEL AVIV MEDICAL CENTER, Tel-Aviv (IL)

(72) Inventors: Arnon Karni, Mevaseret Zion (IL); Karin Bernadet Fainberg, Ramat Gan (IL)

(73) Assignee: THE MEDICAL RESEARCH, INFRASTRUCTURE AND HEALTH SERVICES FUND OF THE TEL AVIV MEDICAL CENTER, Tel-Aviv (IL)

( * ) Notice: Subject to any disclaimer, the term of this patent is extended or adjusted under 35 U.S.C. 154(b) by 40 days.

(21) Appl. No.: 16/606,114

(22) PCT Filed: Apr. 26, 2018

(86) PCT No.: PCT/IL2018/050463
§ 371 (c)(1),
(2) Date: Oct. 17, 2019

(87) PCT Pub. No.: WO2018/198123
PCT Pub. Date: Nov. 1, 2018

(65) Prior Publication Data
US 2020/0046680 A1    Feb. 13, 2020

(30) Foreign Application Priority Data
Apr. 26, 2017  (IL) .......................................... 251949

(51) Int. Cl.
| A61K 31/381 | (2006.01) |
| A61K 31/425 | (2006.01) |
| A61K 31/44  | (2006.01) |
| A61K 31/42  | (2006.01) |
| A61K 31/395 | (2006.01) |
| A61K 31/4178| (2006.01) |
| A61K 31/435 | (2006.01) |
| A61K 31/165 | (2006.01) |
| A61K 31/345 | (2006.01) |
| A61P 25/28  | (2006.01) |
| A61P 25/00  | (2006.01) |

(52) U.S. Cl.
CPC ............ *A61K 31/381* (2013.01); *A61P 25/28* (2018.01)

(58) Field of Classification Search
CPC .... A61K 31/381; A61K 31/425; A61K 31/44; A61K 31/42; A61K 31/395; A61K 31/4178; A61K 31/435; A61K 31/165; A61K 31/345; A61P 25/28; A61P 25/00
See application file for complete search history.

(56) References Cited

U.S. PATENT DOCUMENTS

| 2004/0039037 A1 | 2/2004 | Zhang |
| 2006/0217390 A1 | 9/2006 | Gunic |
| 2008/0249038 A1 | 10/2008 | Feinstein |
| 2015/0139983 A1 | 5/2015 | Karni |

FOREIGN PATENT DOCUMENTS

| EP | 0578246 A1 | 1/1994 |
| EP | 1074551 A2 | 2/2001 |
| WO | 0123382 A1 | 4/2001 |
| WO | 03105857 A1 | 12/2003 |
| WO | 2004083206 A1 | 9/2004 |
| WO | 2006124874 A2 | 11/2006 |
| WO | 2008024302 A2 | 2/2008 |
| WO | 2008118626 A2 | 10/2008 |
| WO | 2011019678 A1 | 2/2011 |
| WO | 2013186777 A2 | 12/2013 |
| WO | 2014160203 A2 | 10/2014 |
| WO | 2016025129 A1 | 2/2016 |

OTHER PUBLICATIONS

National Center for Biotechnology Information. "PubChem Bioassay Record for AID 1044 (2008), Source: The Scripps Research Institute Molecular Screening Center" PubChem, https://pubchem.ncbi.nlm.nih.gov/bioassay/1044 p. 1-15; Accessed Jan. 13, 2021.*
National Center for Biotechnology Information. "PubChem Bioassay Record for AID 540299 (2011), Source: ICCB-Longwood Screening Facility, Harvard Medical School" PubChem, https://pubchem.ncbi.nlm.nih.gov/bioassay/540299 p. 1-12; Accessed Jan. 13, 2021.*
Ascherio, A., "The initiation and prevention of multiple sclerosis." Nature Reviews Neurology 8.11 (2012): 602-612.*
Eixarch, H., "Bone morphogenetic proteins in multiple sclerosis: role in neuroinflammation." Brain, Behavior, and Immunity 68 (2018 ): 1-10.*
McKim, A. S., "Dimethyl sulfoxide USP, PhEur in approved pharmaceutical products and medical devices." Pharmaceutical Technology 32.5 (2008): 74.*
Bani-Yaghoub et al., (2000) The effects of bone morphogenetic protein 2 and 4 (BMP2 and BMP4) on gap junctions during neurodevelopment. Exp Neurol 162(1): 13-26.
Boergermann et al., (2010) Dorsomorphin and LDN-193189 inhibit BMP-mediated Smad, p38 and Akt signalling in C2C12 cells. Int J Biochem Cell Biol 42(11): 1802-1807.
Cheng et al., (2007) Bone morphogenetic protein signaling and olig1/2 interact to regulate the differentiation and maturation of adult oligodendrocyte precursor cells. Stem Cells 25(12): 3204-3214.

(Continued)

*Primary Examiner* — John M Mauro
(74) *Attorney, Agent, or Firm* — Rothwell, Figg, Ernst & Manbeck, P.C.

(57) ABSTRACT

This invention provides small organic molecules useful as therapeutics of neurodegenerative diseases. Small organic molecules that act as inhibitors of bone morphogenetic proteins (BMPs) are useful in the treatment of neuroinflammatory disorders, in particular multiple sclerosis.

10 Claims, 16 Drawing Sheets

(56) References Cited

OTHER PUBLICATIONS

Fainberg et al.,; "Blockage of BMP-2 Signaling, either by Neutralizing Ab, or by Small Molecules, Ameliorates Relapsing—Experimental Autoimmune Encephalomyelitis by Induction of Neurogenesis and Oligodendrogenesis". Poster presented at: MSParis2017, 7th Joint ECTRIMS-ACTRIMS Meeting, Oct. 25-28, 2017, Paris, France. Retrieved from: http://onlinelibrary.ectrims-congress.eu/ectrims/2017/ACTRIMS-ECTRIMS2017/200837/arnon.karni.blockage.of.bmp-2.signaling.either.by.neutralizing.ab.or.by.small.html; 11 pages.
Gomes et al., (2003) Transgenic overexpression of BMP4 increases astroglial and decreases oligodendroglial lineage commitment. Dev Biol 255(1): 164-177.
Grinspan (2015) Bone Morphogenetic Proteins: Inhibitors of Myelination in Development and Disease. Vitam Horm 99: 195-222 abstract.
Gross et al., (1996) Bone morphogenetic proteins promote astroglial lineage commitment by mammalian subventricular zone progenitor cells. Neuron 17(4): 595-606.
Hong and Yu (2009) Applications of small molecule BMP inhibitors in physiology and disease. Cytokine Growth Factor Rev 20(5-6): 409-418.
Karni Arnon; "Small Organic Molecules for use in the treatment neuroinflammatory disorders, in particular multiple sclerosis"; May 2017 (May 2017). Retrieved from: https://www.tasmc.org.il/sites/en/Research/Tech-Transfer/Documents/201705%20Abstract%20Karni%20Final.pdf, on Apr. 24, 2018; 1 page.
Karni Arnon; "Induction of repair by oligodendrogenesis and neurogenesis in immune mediated diseases of central nervous system". The 16th MIXiii-BIOMED National Life Sciences & Technology Week, May 23-25, 2017 | David InterContinental Tel Aviv, Israel. Retrieved from: http://kenes-exhibitions.com/old/biomed2017/wp-content/uploads/2017/04/Arnon-Karni-_Abstract.pdf; Abstract.
Katagiri and Watabe (2016) Bone Morphogenetic Proteins. Cold Spring Harb Perspect Biol 8(6). pii: a021899; 28 pages.
Keller et al, (2004) Molecular recognition of BMP-2 and BMP receptor IA. Nat Struct Mol Biol 11(5): 481-488.
Kurtzke (1983) Rating neurologic impairment in multiple sclerosis: an expanded disability status scale (EDSS). Neurology 33(11): 1444-1452.

Li et al., (2008) Decreased hippocampal cell proliferation correlates with increased expression of BMP4 in the APPswe/PS1DeltaE9 mouse model of Alzheimer's disease. Hippocampus 18(7): 692-698 abstract.
Lim et al., (2000) Noggin antagonizes BMP signaling to create a niche for adult neurogenesis. Neuron 28(3): 713-726.
Mabie et al., (1997) Bone morphogenetic proteins induce astroglial differentiation of oligodendroglial-astroglial progenitor cells. J Neurosci 17(11): 4112-4120.
Sanvitale et al., (2013) A new class of small molecule inhibitor of BMP signaling. PLoS One 8(4): e62721; 11 pages.
Trapp and Nave (2008) Multiple sclerosis: an immune or neurodegenerative disorder? Annu Rev Neurosci 31: 247-269 abstract.
Varaprasad et al., (2006) Discovery of 3-hydroxy-4-carboxyalkylamidino-5-arylamino-isothiazoles as potent MEK1 inhibitors. Bioorg Med Chem Lett 16(15): 3975-3980.
Vittoria Simonini et al., (2010) Regulation of oligodendrocyte progenitor cell maturation by PPARδ: effects on bone morphogenetic proteins. ASN Neuro 2(1): e00025; 13 pages.
CAS Registry No. 882268-63-5; CA Index Name: 2-Thiophenecarboxylic acid, 3-[2-[cyano(2-thienylsulfonyl)methylene]hydrazinyl]-, methyl ester; Source of Registration:Chemical Library, Supplier. Interchim; Entered STN: Apr. 30, 2006; 3 pages.
CAS Registry No. 882278-00-4; CA Index Name: 2-Thiophenecarboxylic acid, 4-cyano-3-[2-[2-thienylsulfonyl)methylene]hydrazinyl]-, methyl ester; Entered STN: Apr. 30, 2006; 3 pages.
PubChem CID: 2820255; IUPAC Name: methyl 3-[2-[cyano(thiophen-2-ylsulfonyl)methylidene]hydrazinyl]thiophene-2-carboxylate; Create Date: Jul. 19, 2005. URL: <https://pubchem.ncbi.nlm.nih.gov/compound/2820255>.Jul. 19, 2005; 10 pages.
PubChem CID: 5715625; IUPAC Name: methyl 3-[(2Z)-2-[cyano(thiophen-2-ylsulfonyl)methylidene]hydrazinyl]thiophene-2-carboxylate; Create Date: Jul. 19, 2005. URL: <https://pubchem.ncbi.nlm.nih.gov/compound/5715625>.Jul. 19, 2005; 11 pages.
PubChem CID: 6371770; IUPAC Name: methyl 3-[(2E)-2-[cyano(thiophen-2-ylsulfonyl)methylidene]hydrazinyl]thiophene-2-carboxylate; Create Date: Sep. 9, 2005. URL: <https://pubchem.ncbi.nlm.nih.gov/compound/6371770>.Sep. 9, 2005; 12 pages.
PubChem CID: 6376145; IUPAC Name: methyl 4-cyano-3-[(2E)-2-[cyano(thiophen-2-ylsulfonyl)methylidene]hydrazinyl]thiophene-2-carboxylate; Create Date: Sep. 11, 2005. URL:<https://pubchem.ncbi.nlm.nih.gov/compound/6376145>.Sep. 11, 2005; 12 pages.

* cited by examiner

SMALL ORGANIC MOLECULES FOR USE IN THE TREATMENT OF NEUROINFLAMMATORY DISORDERS

CROSS REFERENCE TO RELATED APPLICATION

This application is a 35 U.S.C. 371 National Phase Entry Application from PCT/IL2018/050463, filed Apr. 26, 2018, which claims priority to Israel Patent Application No. 251949 filed on Apr. 26, 2017, the disclosures of which are incorporated herein in their entirety by reference.

FIELD OF THE INVENTION

This invention relates to the field of therapeutics of neurodegenerative and neuroinflammatory diseases. Small organic molecules that may act as inhibitors of bone morphogenetic proteins (BMPs) are disclosed as useful in the treatment of neuroinflammatory disorders, in particular multiple sclerosis.

BACKGROUND OF THE INVENTION

Multiple sclerosis (MS) is a widely known demyelinating disease in which the myelin, the insulating covers of nerve cells, in the brain and spinal cord are damaged [1]. Bone morphogenetic proteins (BMPs) were implicated as inhibitors of myelination during development and disease states (reviewed in [2]).

WO 2013/186777 [17] discloses pharmaceutical compositions for the treatment of neuroinflammatory or neurodegenerative diseases comprising a single or a combination of several blocking agent(s) of BMP signaling.

US 2015/139983 [3] discloses methods for the treatment of neuroinflammatory or neurodegenerative diseases comprising a single or a combination of several antibodies directed against BMP-2 and BMP-4.

US 2008/0249038 [4] discloses a method of alleviation or reduction of the symptoms and signs associated with damaged neuronal tissues, whether resulting from tissue trauma, or from chronic or acute degenerative changes, using a BMP2A inhibitor, in particular siRNA molecules or antisense molecules.

Simonini et al. [5] examined effects of the PPARδ (peroxisome proliferator-activated receptors) agonist GW0742 on OPCs (oligodendrocyte progenitor cells), and showed that GW0742 reduced BMP2 and BMP4 mRNA levels in OPCs, with lesser effects in astrocytes. Simonini et al. concluded that PPARδ plays a role in OPC maturation, mediated, in part, by regulation of BMP and BMP antagonists.

Li et al. [6] evaluated hippocampal cell proliferation in the DG subgranular zone (DG-SGZ), and BMP4 mRNA level, in the APPswe/PS1DeltaE9 transgenic mouse, a mouse model of Alzheimer's disease. The investigators found a significant correlation between an increased BMP4 mRNA expression and a decreased number of BrdU labeled cells and suggested that the increased expression of BMP4 mRNA within the DG of the hippocampus may contribute to the decrease in cell proliferation in APPswe/PS1DeltaE9 transgenic mice.

Mabie et al [7] report that the BMPs promote the selective, dose-dependent differentiation of oligodendroglial-astroglial progenitor cells (O-2As) into astrocytes with concurrent suppression of oligodendroglial differentiation.

Gross et al [8] demonstrate that BMPs, cause the selective, dose-dependent elaboration of the astroglial lineage from murine embryonic subventricular zone (SVZ) multipotent progenitor cells.

Gomes et al [9] constructed transgenic mice that overexpress BMP4. The overexpression of BMP4 resulted in a remarkable increase in the density of astrocytes in multiple brain regions accompanied by a decrease in the density of oligodendrocytes. No changes in neuron numbers or the pattern of myelination were detected, and there were no gross structural abnormalities. These observations suggest that BMP4 directs progenitor cells in vivo to commit to the astrocytic rather than the oligodendroglial lineage and that BMPs are likely important mediators of astrocyte development in vivo.

Lim et al [10] show that the BMP antagonist Noggin is expressed by ependymal cells adjacent to the subventricular zone (SVZ). SVZ cells were found to express BMPs as well as their cognate receptors. Purified mouse Noggin protein promoted neurogenesis in vitro and inhibited glial cell differentiation and ectopic Noggin promoted neuronal differentiation of SVZ cells grafted to the striatum. The investigators thus proposed that ependymal Noggin production creates a neurogenic environment in the adjacent SVZ by blocking endogenous BMP signaling.

WO 11/019678 [11] discloses the use of isothiazoles for treating conditions of the eye, e.g. age related macular degeneration. US 2006/217390 [12] discloses cycloalkyl, aryl and heteroaryl amino isothiazoles for the treatment of hepatitis C. WO 03/105857 [13] discloses pharmaceutical compositions containing active compounds, which inhibit the activity of the chemokines, MIP-1 alpha and RANTES. It is also directed to methods of treating inflammatory diseases using these pharmaceutical compositions. US 2004/039037 [14] discloses substituted isothiazole compounds directed towards inhibition of various protein kinases (especially MEK and/or ERK). It is also directed to methods of treatment of diseases associated with abnormality in MEK and/or ERK function.

There remains a need for improved treatments for multiple sclerosis.

SUMMARY OF THE INVENTION

It is now disclosed for the first time that small organic molecules may act as inhibitors of bone morphogenetic proteins (BMPs) including but not limited to BMP2. It is further disclosed that molecules that are selected on the basis of their ability to inhibit BMPs are useful in the treatment of neuroinflammatory disorders, in particular multiple sclerosis. According to some aspects of the invention, small organic molecules capable of inhibiting BMP2 with an IC50 lower than 10 μM are provided. According to further aspects of the invention, small organic molecules capable of inhibiting both BMP2 and BMP4 are provided. According to yet further aspects small organic molecules capable of inhibiting BMP2 are provided in pharmaceutical compositions useful for the treatment neuroinflammatory diseases, including but not limited to multiple sclerosis.

The present invention is based in part on the finding that small organic compounds of the Formulas (I)-(IX), including specific compounds designated herein SM1, SM6, SM7 and SM9 inhibited the activity of bone morphogenetic protein 2 (BMP2) in a cell based assay. Furthermore, these molecules inhibited disease progression in an animal model of relapsing/remitting experimental autoimmune encephalomyelitis (RR-EAE), a well-established model mimicking multiple sclerosis (MS). Without wishing to be bound by any particular theory of a mechanism of action, these small organic molecules appear to induce neurogenesis and oligodendrogenesis, and to maintain the amount of myelin, by inhibiting demyelination, inducing remyelination, or both.

According to some embodiments, the present invention provides a pharmaceutical composition comprising a compound having the general Formula (I) or a salt thereof:

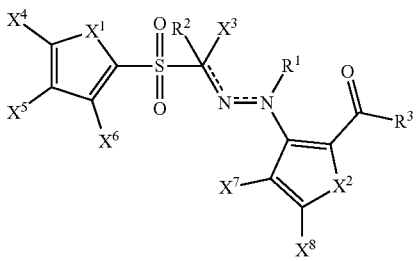

(I)

wherein $X^1$ and $X^2$ are each independently S, O or N—$R^4$, wherein $R^4$ is selected from the group consisting of H, alkyl, cycloalkyl, aryl and heteroaryl;

$X^3$ is selected from the group consisting of CN, halogen, nitro, CO—$X^9$ and $SO_2X^9$, wherein $X^9$ is selected from the group consisting of OH, O⁻ and $NH_2$;

$X^4$, $X^5$, $X^6$, $X^7$, and $X^8$ are each independently selected from the group consisting of H, alkyl, cycloalkyl, aryl, amine, halogen, alkoxy, hydroxy, heteroaryl, CN, nitro, CO—$X^{10}$ and $SO_2X^{10}$, wherein $X^{10}$ is selected from the group consisting of OH, O⁻ and $NH_2$;

one of $R^1$ and $R^2$ is absent and the other $R^1$ and $R^2$ is selected from the group consisting of H, alkyl, cycloalkyl, aryl, amine, halogen, alkoxy, heteroaryl, CN, CO—$X^{11}$ and $SO_2X^{11}$, wherein $X^{11}$ is selected from the group consisting of OH, O⁻ and $NH_2$;

$R^3$ is selected from the group consisting of $OR^5$, O⁻ and $NR^6R^7$, wherein $R^5$, $R^6$, and $R^7$ are each independently selected from the group consisting of H, alkyl, cycloalkyl and aryl; and wherein each of the dotted lines independently represents a single or a double bond.

According to some embodiments, the pharmaceutical composition comprises the compound of Formula (Ia) or a salt thereof:

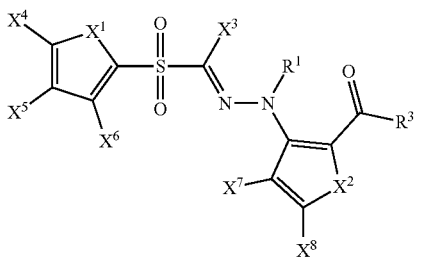

(Ia)

According to some embodiments, there is provided a method of treating a neuroinflamimatory disease, the method comprising the step of administering to a subject in need thereof a therapeutically effective amount of a compound having the general Formula (I) or a salt thereof, wherein each one of $X^1$, $X^2$, $X^3$, $X^4$, $X^5$, $X^6$, $X^7$, $X^8$, $R^1$, $R^2$ and $R^3$ is as described herein.

According to some embodiments, there is provided a method of treating a neuroinflammatory disease, the method comprising the step of administering to a subject in need thereof a therapeutically effective amount of a compound having the general Formula (Ia) or a salt thereof, wherein each one of $X^1$, $X^2$, $X^3$, $X^4$, $X^5$, $X^6$, $X^7$, $X^8$, $R^1$ and $R^3$ is as described herein.

According to some embodiments, there is provided a use of a compound having the general Formula (I) or a salt thereof wherein each one of $X^1$, $X^2$, $X^3$, $X^4$, $X^5$, $X^6$, $X^7$, $X^8$, $R^1$, $R^2$ and $R^3$ are as described for the treatment of a subject suffering from a neuroinflammatory disease.

According to some embodiments, $X^1$ and $X^2$ are both S.
According to some embodiments, $X^3$ is CN.
According to some embodiments, each one of $X^4$, $X^5$, $X^6$, $X^7$, and $X^8$ is H
According to some embodiments, $R^1$ is H.
According to some embodiments, wherein $R^3$ is $OR^5$.
According to some embodiments, $R^5$ is methyl or ethyl.
According to some embodiments, the compound is having the formula SM1:

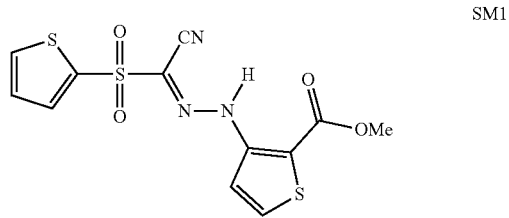 [SMILES: COC(=O)c1sccc1N/N=C(\C#N)S(=O)(=O)c1cccs1]

SM1

According to some embodiments, there is provided a pharmaceutical composition comprising a compound having the general Formula (IX) or a salt thereof:

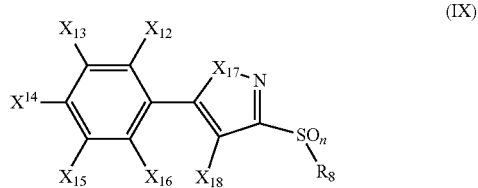

(IX)

wherein $X^{12}$, $X^{13}$, $X^{15}$ and $X^{16}$ are each independently selected from the group consisting of H, alkyl, cycloalkyl, aryl, amine, halogen, alkoxy, hydroxy, heteroaryl, CN, $NO_2$, CO—$X^{19}$ and $SO_2X^{19}$, wherein $X^{19}$ is selected from the group consisting of OH, O⁻ and $NH_2$;

$X^{14}$, and $X^{is}$ are each independently selected from the group consisting of H, alkyl, cycloalkyl, aryl, amine, halogen, alkoxy, hydroxy, heteroaryl, CN, $NO_2$, CO—$X^{20}$ and $SO_2X^{20}$, wherein $X^{20}$ is selected from the group consisting of OH, O⁻ and $NH_2$;

$X^{17}$ is S, O or N—$R^9$, wherein $R^9$ is selected from the group consisting of H, alkyl, cycloalkyl, aryl and heteroaryl;

n is 1 or 2; and $R^8$ is selected from the group consisting of alkyl, halogenated alkyl, cycloalkyl and aryl;

for use in the treatment of a neuroinflammatory disease.

According to some embodiments, there is provided a method of treating a neuroinflammatory disease, the method comprising the step of administering to a subject in need thereof a therapeutically effective amount of a compound having the general Formula (IX) or a salt thereof, wherein each one of $X^{12}$, $X^{13}$, $X^{14}$, $X^{15}$, $X^{16}$, $X^{17}$, $X^{18}$ and $R^8$ is as described herein.

According to some embodiments, there is provided a use of a compound having the general Formula (IX) or a salt thereof and a pharmaceutically acceptable carrier, in the preparation of a pharmaceutical composition for the treatment of a subject suffering from a neuroinflammatory disease, wherein each one of $X^{12}$, $X^{13}$, $X^{14}$, $X^{15}$, $X^{16}$, $X^{17}$, $X^{18}$ and $R^8$ is as described herein.

According to some embodiments, each one of $X^{12}$, $X^{13}$, $X^{15}$ and $X^{16}$ is H.

According to some embodiments, $X^{14}$ is a halogen.

According to some embodiments, $X^{14}$ is a Cl.

According to some embodiments, $X^{18}$ is CN.

According to some embodiments, $X^{17}$ is O.

According to some embodiments, $R^8$ is methyl.

According to some embodiments, n is 2.

According to some embodiments, the compound is having the formula SM9:

SM9

According to some embodiments, there is provided a pharmaceutical composition comprising a compound having the general Formula SM7, an ester or a salt thereof:

SM7 for use in the treatment of a neuroinflammatory disease.

According to some embodiments, there is provided a pharmaceutical composition comprising a compound having the general Formula SM6, or a salt thereof:

SM6

According to some embodiments, there is provided a pharmaceutical composition comprising a compound having the general Formula SM2, or a salt thereof:

SM2 for use in the treatment of a neuroinflammatory disease.

According to some embodiments, there is provided a pharmaceutical composition comprising a compound having the general Formula SM3, or a salt thereof:

SM3

According to some embodiments, there is provided a pharmaceutical composition comprising a compound having the general Formula SM4, or a salt thereof:

SM4

According to some embodiments, there is provided a pharmaceutical composition comprising a compound having the general Formula SM5, or a salt thereof:

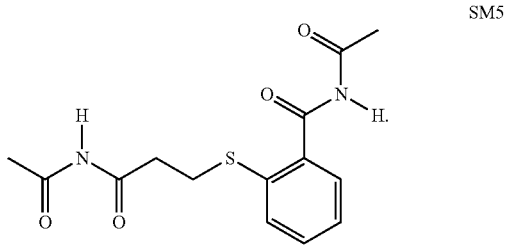

SM5

According to some embodiments, there is provided a pharmaceutical composition comprising a compound having the general Formula SM8, or a salt thereof:

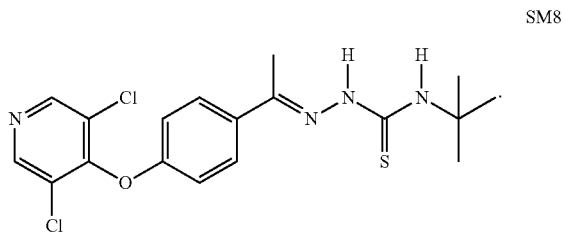

SM8

According to some embodiments, the pharmaceutical composition is for use in the treatment of a neuroinflammatory disease.

According to some embodiments, the pharmaceutical composition further comprises an additional therapeutic agent.

According to some embodiments, the neuroinflammatory disease is multiple sclerosis.

According to some embodiments, the multiple sclerosis is relapsing remitting multiple sclerosis.

According to some embodiments, the method further comprises the administration of an additional therapeutic agent to said subject.

According to some embodiments, the additional therapeutic agent is administered prior to, concomitantly, or following the administration of the at least one compound, or a pharmaceutical composition comprising said at least one compound.

BRIEF DESCRIPTION OF THE FIGURES

In order to better understand the subject matter that is disclosed herein and to exemplify how it may be carried out in practice, embodiments will now be described, by way of non-limiting example only, with reference to the accompanying drawings, in which.

DETAILED DESCRIPTION OF THE INVENTION

Figure 1A:
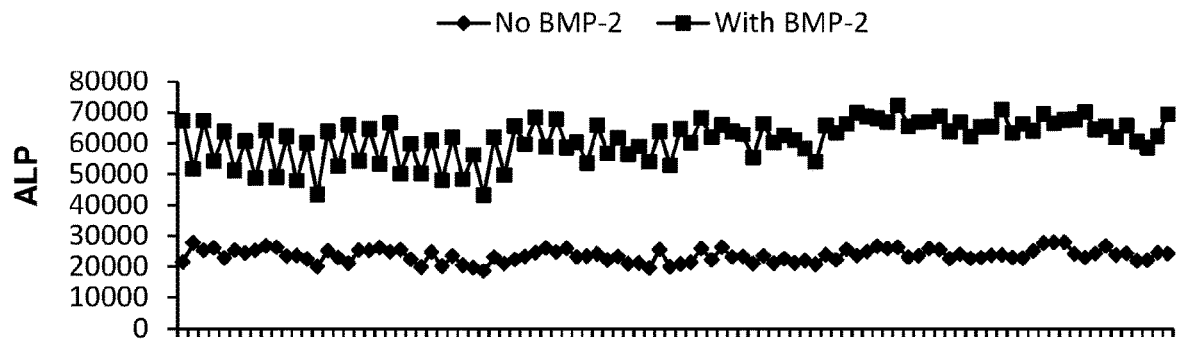
FIG. 1—High Throughput Screening (HTS) Bioassay evaluation. (A) ALP activity, determined by CDP-Star® chemiluminescent substrate, presented as O.D$_{405\,nm}$ per well, in the presence or absence of BMP-2 ("with BMP-2"—squares, "No BMP-2"—diamonds). (B) Cell viability, determined by Cell Titer-Glo® Luminescent substrate, presented as O.D$_{405\,nm}$ per well, in the presence or absence of BMP-2 ("with BMP-2"—squares, "No BMP-2"—diamonds). (C) The ratio of ALP/cell per well in the presence or absence of BMP-2 ("with BMP-2"—squares, "No BMP-2"—diamonds).

The present invention provides small organic molecules capable of inhibiting BMPs that show therapeutic utility in inhibiting EAE, in particular a relapsing form of EAE which is a model mimicking relapsing remitting multiple sclerosis.

The present invention is based in part on the finding that small organic compounds of the Formulas (I)-(IX), including but not limited to specific compounds designated herein SM1, SM6, SM7 and SM9 inhibited the activity of bone morphogenetic protein 2 (BMP2) in a cell based assay. These molecules were shown to inhibit disease progression in a relapsing/remitting experimental autoimmune encephalomyelitis (RR-EAE) animal model, a well-established model mimicking multiple sclerosis (MS). Without wishing to be bound by any particular theory of a mechanism of action, these molecules appear to induce neurogenesis and oligodendrogenesis, and to maintain the amount of myelin, by inhibiting demyelination, inducing remyelination, or both.

Thus, according to some embodiments, there is provided a pharmaceutical composition comprising a bone morphogenetic protein 2 (BMP2) inhibitor, wherein the BMP2 inhibitor is a small molecule. According to some embodiments, the pharmaceutical composition is for use in the treatment neuroinflammatory diseases, such as multiple sclerosis.

According to some embodiments, there is provided a method for treating a neuroinflammatory disease, the method comprising the step of administering to a subject in need thereof a therapeutically effective amount of a bone morphogenetic protein 2 (BMP2) inhibitor, wherein the BMP2 inhibitor is a small molecule.

According to some embodiments, there is provided a use of bone morphogenetic protein 2 (BMP2) inhibitor in the preparation of a pharmaceutical composition for the treatment of a subject suffering from a neuroinflammatory disease, wherein the BMP2 inhibitor is a small molecule.

According to some embodiments, there is provided a use of bone morphogenetic protein 2 (BMP2) inhibitor for the treatment of a subject suffering from a neuroinflammatory disease, wherein the BMP2 inhibitor is a small molecule.

According to some embodiments, the small molecule is having a molecular weight of no more than 1000 gr/mol.

According to some embodiments, the small molecule is having a formula selected from the group consisting of Formula (I), Formula (II), Formula (III), Formula (IV), Formula (V), Formula (VI), Formula (VII), Formula (VIII), Formula (IX) and salts thereof. According to some embodiments, the small molecule is having a formula selected from the group consisting of Formula (I), Formula (VI), Formula (VII), Formula (IX) and salts thereof. According to some embodiments, the small molecule is having a formula selected from the group consisting of Formula (I), Formula (IX) and salts thereof. According to some embodiments, the small molecule is having a formula selected from the group consisting of SM1, SM2, SM3, SM4, SM5, SM6, SM7, SM8, SM9 and salts thereof. According to some embodiments, the small molecule is having a formula selected from the group consisting of SM1, SM6, SM7, SM9 and salts thereof. According to some embodiments, the small molecule is having a formula selected from the group consisting of SM1, SM9 and salts thereof.

According to some embodiments, the present invention provides a pharmaceutical composition comprising a compound having the general Formula (I) or a salt thereof:

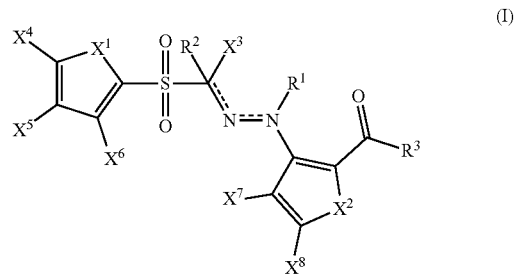

(I)

wherein $X^1$ and $X^2$ are each independently S, O or N—$R^4$, wherein $R^4$ is selected from the group consisting of H, alkyl, cycloalkyl, aryl and heteroaryl;

$X^3$ is selected from the group consisting of CN, halogen, nitro, CO—$X^9$ and $SO_2X^9$, wherein $X^9$ is selected from the group consisting of OH, O⁻ and $NH_2$;

$X^4$, $X^5$, $X^6$, $X^7$, and $X^8$ are each independently selected from the group consisting of H, alkyl, cycloalkyl, aryl, amine, halogen, alkoxy, hydroxy, heteroaryl, CN, nitro, CO—$X^{10}$ and $SO_2X^{10}$, wherein $X^{10}$ is selected from the group consisting of OH, O⁻ and $NH_2$;

one of $R^1$ and $R^2$ is absent and the other $R^1$ and $R^2$ is selected from the group consisting of H, alkyl, cycloalkyl, aryl, amine, halogen, alkoxy, heteroaryl, CN, CO—$X^1$ and $SO_2X^{11}$, wherein $X^{11}$ is selected from the group consisting of OH, O— and $NH_2$;

$R^3$ is selected from the group consisting of $OR^5$, O⁻ and $NR^6R^7$, wherein $R^5$, $R^6$, and $R^7$ are each independently selected from the group consisting of H, alkyl, cycloalkyl and aryl; and wherein each of the dotted lines independently represents a single or a double bond.

According to some embodiments, there is provided a method of treating a neuroinflammatory disease, the method comprising the step of administering to a subject in need thereof a therapeutically effective amount of a compound having the general Formula (I) or a salt thereof, wherein each one of $X^1$, $X^2$, $X^3$, $X^4$, $X^5$, $X^6$, $X^7$, $X^8$, $R^1$, $R^2$ and $R^3$ is as described herein.

According to some embodiments, there is provided a use of a compound having the general Formula (I) or a salt thereof for the treatment of a subject suffering from a neuroinflammatory disease, wherein each one of $X^1$, $X^2$, $X^3$, $X^4$, $X^5$, $X^6$, $X^7$, $X^8$, $R^1$, $R^2$ and $R^3$ is as described herein.

According to some embodiments, the pharmaceutical composition comprises the compound of Formula (Ia) or a salt thereof:

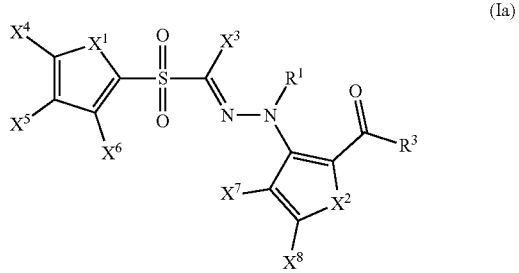

(Ia)

According to some embodiments, there is provided a method of treating a neuroinflammatory disease, the method comprising the step of administering to a subject in need thereof a therapeutically effective amount of a compound having the general Formula (Ia) or a salt thereof, wherein each one of $X^1$, $X^2$, $X^3$, $X^4$, $X^5$, $X^6$, $X^7$, $X^8$, $R^1$ and $R^3$ is as described herein.

According to some embodiments, there is provided a use of a compound having the general Formula (Ia) or a salt thereof for the treatment of a subject suffering from a neuroinflammatory disease, wherein each one of $X^1$, $X^2$, $X^3$, $X^4$, $X^5$, $X^6$, $X^7$, $X^8$, $R^1$ and $R^3$ is as described herein.

According to some embodiments, $X^1$ and $X^2$ are each independently S or O. According to some embodiments, $X^1$ is S or O. According to some embodiments, $X^2$ is S or O. According to some embodiments, $X^1$ is S. According to some embodiments, $X^2$ is S. According to some embodiments, $X^1$ and $X^2$ are both S.

According to some embodiments, $X^3$ is selected from the group consisting of CN, halogen and nitro. According to some embodiments, $X^3$ is CN.

According to some embodiments, $X^4$, $X^5$, $X^6$, $X^7$, and $X^8$ are each independently selected from the group consisting of H, alkyl, halogen, hydroxy and alkoxy. According to some embodiments, $X^4$, $X^5$, $X^6$, $X^7$, and $X^8$ are each independently H or halogen. According to some embodiments, $X^4$ is H. According to some embodiments, $X^5$ is H. According to some embodiments, $X^6$ is H. According to some embodiments, $X^7$ is H. According to some embodiments, $X^8$ is H. According to some embodiments, at least one of $X^4$, $X^5$, $X^6$, $X^7$, and $X^8$ is H. According to some embodiments, at least two of $X^4$, $X^5$, $X^6$, $X^7$, and $X^8$ are H. According to some embodiments, at least three of $X^4$, $X^5$, $X^6$, $X^7$, and $X^8$ are H. According to some embodiments, at least four of $X^4$, $X^5$, $X^6$, $X^7$, and $X^8$ are H. According to some embodiments, $X^4$, $X^5$, $X^6$, $X^7$, and $X^8$ are each independently H.

According to some embodiments, one of $R^1$ and $R^2$ is absent and the other $R^1$ and $R^2$ is selected from the group consisting of H, alkyl, cycloalkyl, aryl, CO—$X^{11}$ and $SO_2X^{11}$. According to some embodiments, $R^2$ is absent and $R^1$ is selected from the group consisting of H, alkyl, cycloalkyl, aryl, CO—$X^{11}$ and $SO_2X$. According to some embodiments, $R^1$ is H.

According to some embodiments, $R^3$ is selected from the group consisting of $OR^5$ and $O^-$. According to some embodiments, $R^3$ is $OR^5$. According to some embodiments, $R^5$ is an alkyl chain. According to some embodiments, $R^5$ is selected from the group consisting of methyl, ethyl, n-propyl, iso-propyl, butyl, n-butyl, sec-butyl and isobutyl. According to some embodiments, $R^5$ is methyl or ethyl. According to some embodiments, $R^5$ is methyl. According to some embodiments, $R^3$ is OMe or OEt. According to some embodiments, $R^3$ is OMe.

According to some embodiments, the compound is having the formula SM1:

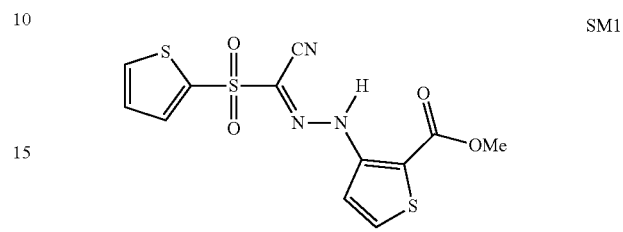

SM1

According to some embodiments, the present invention provides a pharmaceutical composition comprising a compound having the general Formula (IX) or a salt thereof:

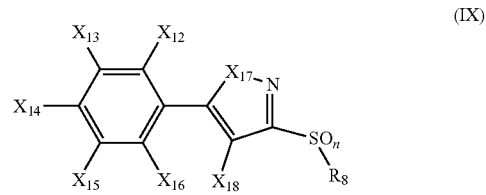

(IX)

wherein
$X^{12}$, $X^{13}$, $X^{15}$ and $X^{16}$ are each independently selected from the group consisting of H, alkyl, cycloalkyl, aryl, amine, halogen, alkoxy, hydroxy, heteroaryl, CN, $NO_2$, CO—$X^{19}$ and $SO_2X^{19}$, wherein $X^{19}$ is selected from the group consisting of OH, $O^-$ and $NH_2$;
$X^{14}$, and X are each independently selected from the group consisting of H, alkyl, cycloalkyl, aryl, amine, halogen, alkoxy, hydroxy, heteroaryl, CN, $NO_2$, CO—$X^{20}$ and $SO_2X^{20}$, wherein $X^{20}$ is selected from the group consisting of OH, $O^-$ and $NH_2$;
$X^{17}$ is S, O or N—$R^9$, wherein $R^9$ is selected from the group consisting of H, alkyl, cycloalkyl, aryl and heteroaryl;
n is 1 or 2; and
$R^8$ is selected from the group consisting of alkyl, halogenated alkyl, cycloalkyl and aryl;
for use in the treatment of a neuroinflammatory disease.

According to some embodiments, there is provided a method of treating a neuroinflammatory disease, the method comprising the step of administering to a subject in need thereof a therapeutically effective amount of a compound having the general Formula (IX) or a salt thereof, wherein each one of $X^{12}$, $X^{13}$, $X^{14}$, $X^{15}$, $X^{16}$, $X^{17}$, $X^{18}$ and $R^8$ is as described herein.

According to some embodiments, there is provided a use of a compound having the general Formula (IX) or a salt thereof for the treatment of a subject suffering from a neuroinflammatory disease, wherein each one of $X^{12}$, $X^{13}$, $X^{14}$, $X^{15}$, $X^{16}$, $X^{17}$, $X^{18}$ and $R^8$ is as described herein.

According to some embodiments, $X^{12}$, $X^{13}$, $X^{15}$ and $X^{16}$ are each independently selected from the group consisting of H, alkyl, cycloalkyl, aryl, amine, halogen, alkoxy, hydroxy CN, and $NO_2$. According to some embodiments, $X^{12}$, $X^{13}$, $X^{15}$ and $X^{16}$ are each independently selected from the group consisting of H, alkyl, halogen, hydroxy and alkoxy. According to some embodiments, $X^{12}$, $X^{13}$, $X^{15}$ and $X^{16}$ are each independently H or halogen. According to some embodiments, $X^{12}$ is H. According to some embodiments, $X^{13}$ is H. According to some embodiments, $X^{15}$ is H. According to some embodiments, $X^{16}$ is H. According to some embodiments, at least one of $X^{12}$, $X^{13}$, $X^{15}$ and $X^{16}$ is H. According to some embodiments, at least two of $X^{12}$, $X^{13}$, $X^{15}$ and $X^{16}$ are H. According to some embodiments, at least three of $X^{12}$, $X^{13}$, $X^{15}$ and $X^{16}$ are H. According to some embodiments, $X^4$, $X^5$, $X^6$, $X^7$, and $X^8$ are each independently H.

According to some embodiments, $X^{14}$ is selected from the group consisting of H, amine, halogen, alkoxy, hydroxy, CN and $NO_2$. According to some embodiments, $X^{14}$ is selected from the group consisting of $NH_2$, halogen, alkoxy, hydroxy, CN and $NO_2$. According to some embodiments, $X^{14}$ is selected from the group consisting of halogen and hydroxy. According to some embodiments, $X^{14}$ is a halogen. According to some embodiments, $X^{14}$ is selected from the group consisting of F and Cl. According to some embodiments, $X^{14}$ is Cl.

According to some embodiments, $X^{18}$ is selected from the group consisting of halogen, CN, $NO_2$, CO—$X^{20}$ and $SO_2X^{20}$, wherein $X^{20}$ is selected from the group consisting of OH, O— and $NH_2$. According to some embodiments, $X^{18}$ is CN.

According to some embodiments, n is 2.

According to some embodiments, $R^8$ is selected from the group consisting of alkyl and halogenated alkyl. According to some embodiments, $R^8$ is an alkyl group. According to some embodiments, $R^8$ is a $C_{1-4}$ alkyl. According to some embodiments, $R^8$ is selected from the group consisting of Me, Et and $CF_3$. According to some embodiments, $R^8$ is Me.

According to some embodiments, the compound is having the formula SM9:

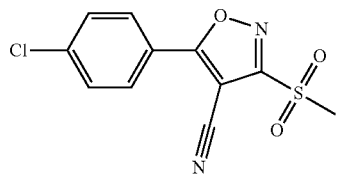

SM9

According to some embodiments, the present invention provides a pharmaceutical composition comprising a compound having the general Formula (VII) or a salt thereof:

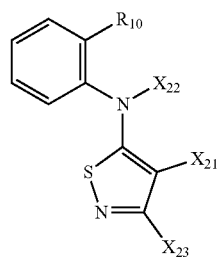

(VII)

wherein
$X^{21}$ and $R^{10}$ are each independently selected from the group consisting of alkyl, halogenated alkyl, cycloalkyl, aryl, amine, halogen, alkoxy, hydroxy, heteroaryl, CN, $NO_2$, CO—$X^{23}$ and $SO_2X^{23}$, wherein $X^{23}$ is selected from the group consisting of OH, O— and $NH_2$;

$X^{22}$ is selected from the group consisting of $OR^{12}$, O— and $NR^{13}R^{14}$, wherein $R^{12}$, $R^{13}$, and $R^{14}$ are each independently selected from the group consisting of H, alkyl, cycloalkyl and aryl; and $R^{11}$ is selected from the group consisting of H, alkyl, cycloalkyl, aryl, amine, halogen, alkoxy, heteroaryl, CN, CO—$X^{24}$ and $SO_2X^{24}$, wherein $X^{24}$ is selected from the group consisting of OH, O— and $NH_2$;

for use in the treatment of a neuroinflammatory disease.

According to some embodiments, there is provided a method of treating a neuroinflammatory disease, the method comprising the step of administering to a subject in need thereof a therapeutically effective amount of a compound having the general Formula (VII) or a salt thereof, wherein each one of $X^{21}$, $X^{22}$, $R^{10}$ and $R^{11}$ is as described herein.

According to some embodiments, there is provided a use of a compound having the general Formula (VII) or a salt thereof for the treatment of a subject suffering from a neuroinflammatory disease, wherein each one of $X^{21}$, $X^{22}$, $R^{10}$ and $R^{11}$ is as described herein.

According to some embodiments, $X^{21}$ is selected from the group consisting of halogen, CN, $NO_2$, CO—$X^{23}$ and $SO_2X^{23}$. According to some embodiments, $X^{21}$ is CN.

According to some embodiments, $X^{22}$ is $OR^{12}$. According to some embodiments, $R^{12}$ is H or alkyl. According to some embodiments, $R^{12}$ is H. According to some embodiments, $X^{22}$ is OH.

According to some embodiments, $R^{10}$ is selected from the group consisting of alkyl, halogenated alkyl, cycloalkyl, and halogen. According to some embodiments, $R^{10}$ is a halogenated alkyl. According to some embodiments, $R^{10}$ is a fluorinated alkyl. According to some embodiments, $R^{10}$ is $CF_3$.

According to some embodiments, $R^{11}$ is selected from the group consisting of H, alkyl, cycloalkyl, aryl, amine, halogen, alkoxy, heteroaryl, CN, CO—$X^{24}$ and $SO_2X^{24}$. According to some embodiments, $R^{11}$ is H or CO—$X^{24}$. According to some embodiments, $R^{11}$ is H.

According to some embodiments, the compound is having the formula SM7:

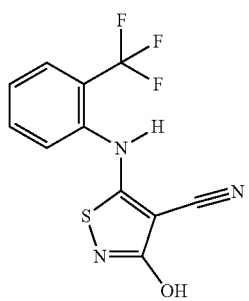

SM7

According to some embodiments, the present invention provides a pharmaceutical composition comprising a compound having the general Formula (VI) or a salt thereof:

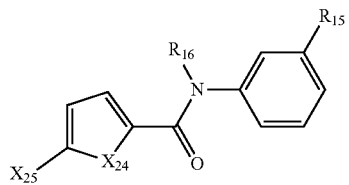

(VI)

wherein

X²⁴ is O or S.

R¹⁵ and X₂₅ are each independently selected from the group consisting of alkyl, halogenated alkyl, cycloalkyl, aryl, amine, halogen, alkoxy, hydroxy, heteroaryl, CN, NO₂, CO—X²⁶ and SO₂X²⁶, wherein X²⁶ is selected from the group consisting of OH, O⁻ and NH₂; and R₁₆ is selected from the group consisting of H, alkyl, cycloalkyl, aryl, amine, halogen, alkoxy, heteroaryl, CN, CO—X²⁴ and SO₂X²⁴, wherein X²⁴ is selected from the group consisting of OH, O⁻ and NH₂.

According to some embodiments, there is provided a method of treating a neuroinflammatory disease, the method comprising the step of administering to a subject in need thereof a therapeutically effective amount of a compound having the general Formula (VI) or a salt thereof, wherein each one of X²⁴, X²⁵, R¹⁵ and R¹⁶ is as described herein.

According to some embodiments, there is provided a use of a compound having the general Formula (VI) or a salt thereof for the treatment of a subject suffering from a neuroinflammatory disease, wherein each one of X²⁴, X²⁵, R¹⁵ and R¹⁶ is as described herein.

According to some embodiments, X²⁴ is O.

According to some embodiments, X₂₅ is selected from the group consisting of amine, halogen, CN, NO₂, CO—X²⁶ and SO₂X²⁶. According to some embodiments, X₂₅ comprises a nitrogen atom. According to some embodiments, X₂₅ is NO₂.

According to some embodiments, R¹⁵ is selected from the group consisting of alkyl, halogenated alkyl, cycloalkyl, and halogen. According to some embodiments, R¹⁵ is a halogenated alkyl. According to some embodiments, R¹⁵ is a fluorinated alkyl. According to some embodiments, R¹⁵ is CF₃.

According to some embodiments, R¹⁶ is selected from the group consisting of H, alkyl, cycloalkyl, aryl, amine, halogen, alkoxy, heteroaryl, CN, CO—X²⁴ and SO₂X²⁴. According to some embodiments, R¹⁶ is H or CO—X²⁴. According to some embodiments, R¹⁶ is H.

According to some embodiments, the compound is having the formula SM6:

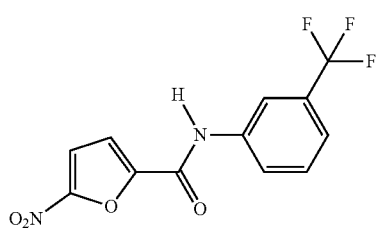

SM6

According to some embodiments, the present invention provides a pharmaceutical composition comprising a compound having the general Formula (II) or a salt thereof:

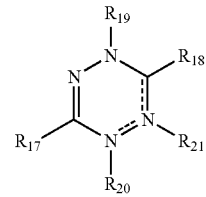

(II)

wherein

R¹⁷ and R¹⁸ are each independently an optionally substituted phenyl ring;

R¹⁹ is selected from the group consisting of H, alkyl, cycloalkyl and aryl;

one of R²⁰ and R²¹ is absent and the other R²⁰ or R²¹ is selected from the group consisting of H, alkyl, cycloalkyl and aryl; and each of the dotted lines independently represents a single or a double bond;

for use in the treatment of a neuroinflammatory disease.

According to some embodiments, the compound is having the general Formula (IIa):

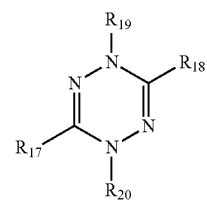

(IIa)

wherein each one of R¹⁷, R¹⁸, R¹⁹, and R²⁰ is as described herein.

According to some embodiments, there is provided a method of treating a neuroinflammatory disease, the method comprising the step of administering to a subject in need thereof a therapeutically effective amount of a compound having the general Formula (II) or a salt thereof, wherein each one of R¹⁷, R¹⁸, R¹⁹, and R²⁰ is as described herein.

According to some embodiments, there is provided a use of a compound having the general Formula (II) or a salt thereof for the treatment of a subject suffering from a neuroinflammatory disease, wherein each one of R¹⁷, R¹⁸, R¹⁹, and R²⁰ is as described herein.

According to some embodiments, R¹⁷ is C₆H₅. According to some embodiments, R¹⁸ is C₆H₅. According to some embodiments, R¹⁷ and R¹⁸ are both C₆H₅.

According to some embodiments, R¹⁹ is H.

According to some embodiments, R²⁰ is H.

According to some embodiments, R²¹ is absent.

According to some embodiments, the compound is having the formula SM2:

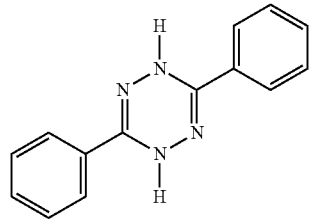

SM2

According to some embodiments, the present invention provides a pharmaceutical composition comprising a compound having the general Formula (III) or a salt thereof:

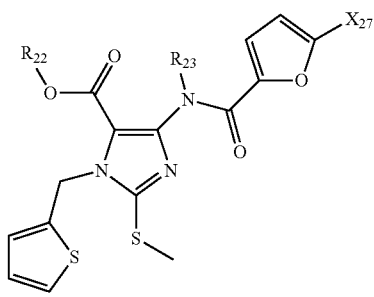

(III)

wherein $R^{22}$ and $R^{23}$ are each independently selected from the group consisting of H, alkyl, cycloalkyl and aryl; and $X^{27}$ is selected from the group consisting of halogenated alkyl, amine, halogen, alkoxy, hydroxy, CN and $NO_2$.

According to some embodiments, there is provided a method of treating a neuroinflammatory disease, the method comprising the step of administering to a subject in need thereof a therapeutically effective amount of a compound having the general Formula (III) or a salt thereof, wherein each one of $X^{27}$, $R^{22}$ and $R^{23}$ is as described herein.

According to some embodiments, there is provided a use of a compound having the general Formula (III) or a salt thereof for the treatment of a subject suffering from a neuroinflammatory disease, wherein each one of $X^{27}$, $R^{22}$ and $R^{23}$ is as described herein.

According to some embodiments, $X_{27}$ comprises a nitrogen atom. According to some embodiments, $X_{27}$ is $NO_2$.

According to some embodiments, $R^{22}$ is an alkyl chain. According to some embodiments, $R^{22}$ is selected from the group consisting of methyl, ethyl, n-propyl, isopropyl, butyl, n-butyl, sec-butyl and isobutyl. According to some embodiments, $R^{22}$ is methyl or ethyl. According to some embodiments, $R^{22}$ is ethyl.

According to some embodiments, $R^{23}$ is H.

According to some embodiments, the compound is having the formula SM3:

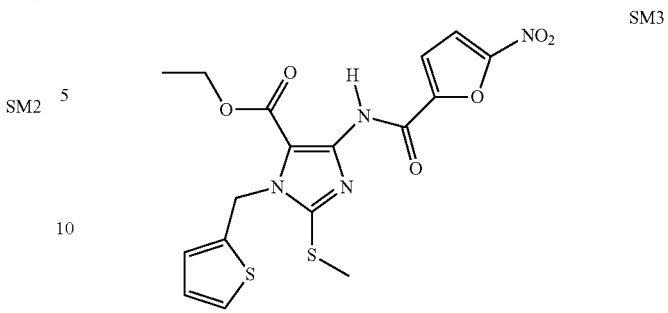

SM3

According to some embodiments, the present invention provides a pharmaceutical composition comprising a compound having the general Formula (IV) or a salt thereof:

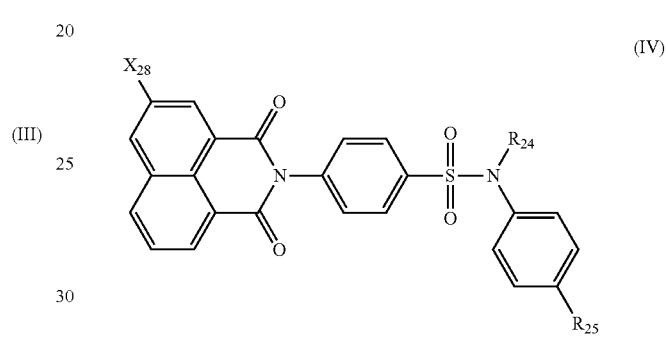

(IV)

wherein $X^{28}$ is selected from the group consisting of halogenated alkyl, amine, halogen, alkoxy, hydroxy, CN and $NO_2$.

$R^{24}$ is selected from the group consisting of H, alkyl, cycloalkyl and aryl; and $R^{25}$ is selected from the group consisting of alkyl, halogenated alkyl, cycloalkyl, aryl, amine, halogen, alkoxy, hydroxy, heteroaryl, CN and $NO_2$.

According to some embodiments, there is provided a method of treating a neuroinflammatory disease, the method comprising the step of administering to a subject in need thereof a therapeutically effective amount of a compound having the general Formula (IV) or a salt thereof, wherein each one of $X^{28}$, $R^{24}$ and $R^{25}$ is as described herein.

According to some embodiments, there is provided a use of a compound having the general Formula (IV) or a salt thereof for the treatment of a subject suffering from a neuroinflammatory disease, wherein each one of $X^{28}$, $R^{24}$ and $R^{25}$ is as described herein.

According to some embodiments, $X_{28}$ comprises a nitrogen atom. According to some embodiments, $X_{28}$ is $NO_2$.

According to some embodiments, $R^{24}$ is H.

According to some embodiments, $R^{25}$ is selected from the group consisting of alkyl, halogenated alkyl, cycloalkyl, and halogen. According to some embodiments, $R^{25}$ is a halogenated alkyl. According to some embodiments, $R^{25}$ is a fluorinated alkyl. According to some embodiments, $R^{25}$ is $CF_3$.

According to some embodiments, the compound is having the formula SM4:

SM4

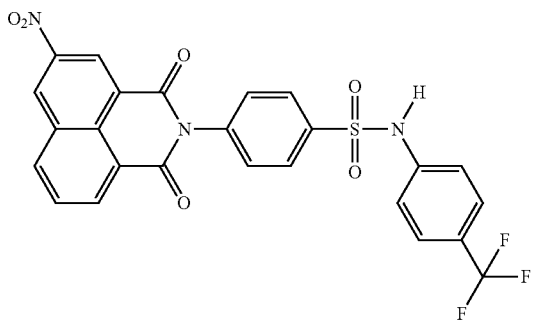

According to some embodiments, the present invention provides a pharmaceutical composition comprising a compound having the general Formula (V) or a salt thereof:

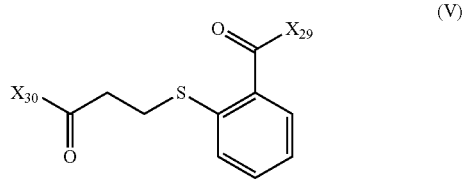

(V)

wherein
$X^{29}$ is selected from the group consisting of $OR^{26}$, O— and $NR^{27}R^{28}$, wherein $R^{26}$, $R^{27}$, and $R^{28}$ are each independently selected from the group consisting of H, $COR^{29}$ alkyl, cycloalkyl and aryl, wherein $R^{29}$ is selected from the group consisting of H, alkyl, cycloalkyl and aryl; and $X^{30}$ is selected from the group consisting of $OR^{30}$, O- and $NR^{31}R^{32}$, wherein $R^{30}$, $R^{31}$, and $R^{32}$ are each independently selected from the group consisting of H, $COR^{33}$, alkyl, cycloalkyl and aryl, wherein $R^{33}$ is selected from the group consisting of H, alkyl, cycloalkyl and aryl.

According to some embodiments, there is provided a method of treating a neuroinflammatory disease, the method comprising the step of administering to a subject in need thereof a therapeutically effective amount of a compound having the general Formula (V) or a salt thereof, wherein each one of $X^{29}$, and $X^{30}$ is as described herein.

According to some embodiments, there is provided a use of a compound having the general Formula (V) or a salt thereof for the treatment of a subject suffering from a neuroinflammatory disease, wherein each one of $X^{29}$, and $X^{30}$ is as described herein.

According to some embodiments, $X^{29}$ is $NR^{27}R^{28}$. According to some embodiments, $R^{27}$ is H. According to some embodiments, $R^{28}$ is $COR^{29}$. According to some embodiments, $R^{29}$ is an alkyl group. According to some embodiments, $R^{29}$ is a $C_{1-4}$ alkyl. According to some embodiments, $R^{29}$ is a methyl. According to some embodiments, $X^{29}$ is NHAc.

According to some embodiments, $X^{30}$ is $NR^{31}R^{32}$. According to some embodiments, $R^{31}$ is H. According to some embodiments, $R^{32}$ is $COR^{33}$. According to some embodiments, $R^{33}$ is an alkyl group. According to some embodiments, $R^{33}$ is a $C_{1-4}$ alkyl. According to some embodiments, $R^{33}$ is a methyl. According to some embodiments, $X^{33}$ is NHAc.

According to some embodiments, the compound is having the formula SM5:

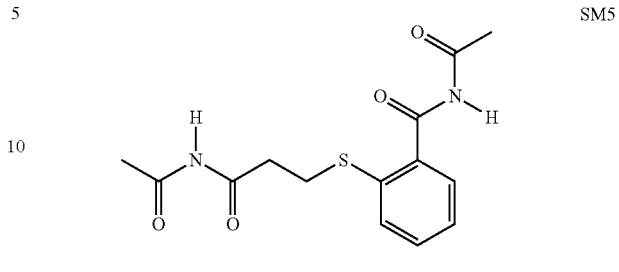

SM5

According to some embodiments, the present invention provides a pharmaceutical composition comprising a compound having the general Formula (VIII) or a salt thereof:

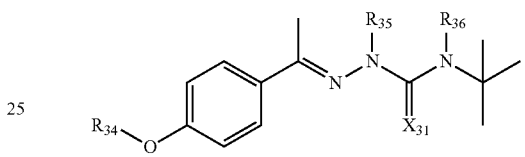

(VIII)

wherein
$X^{31}$ is selected from S and O;
$R^{34}$ is selected from halogenated aryl and halogenated heteroaryl; and
$R^{35}$ and $R^{36}$ are each independently selected from the group consisting of H, alkyl, cycloalkyl and aryl.

According to some embodiments, there is provided a method of treating a neuroinflammatory disease, the method comprising the step of administering to a subject in need thereof a therapeutically effective amount of a compound having the general Formula (VIII) or a salt thereof, wherein each one of $X^{31}$, $R^{34}$, $R^{35}$ and $R^{36}$ is as described herein.

According to some embodiments, there is provided a use of a compound having the general Formula (VIII) or a salt thereof for the treatment of a subject suffering from a neuroinflammatory disease, wherein each one of $X^{31}$, $R^{34}$, $R^{35}$ and $R^{36}$ is as described herein.

According to some embodiments, $X^{31}$ is S.

According to some embodiments, $R^{34}$ is a halogenated heteroaryl. According to some embodiments, $R^{34}$ comprises at least two halogen atoms. According to some embodiments, $R^{34}$ comprises two halogen atoms. According to some embodiments, the halogen atoms are chlorine atoms. According to some embodiments, $R^{34}$ is a halogenated pyridine. According to some embodiments, $R^{34}$ is:

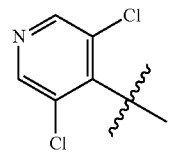 [SMILES: *c1c(Cl)cncc1Cl]

According to some embodiments, $R^{35}$ is H. According to some embodiments, $R^{36}$ is H. According to some embodiments, both $R^{35}$ and $R^{36}$ are H.

According to some embodiments, the compound is having the formula SM8:

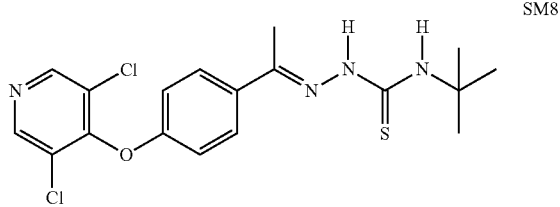 [SMILES: C/C(=N\NC(=S)NC(C)(C)C)c1ccc(Oc2c(Cl)cncc2Cl)cc1]

SM8

According to some embodiments, the pharmaceutical composition is for use in the treatment of a neuroinflammatory disease.

According to some embodiments, the pharmaceutical composition further comprises an additional therapeutic agent.

According to some embodiments, the neuroinflammatory disease is multiple sclerosis.

According to some embodiments, the multiple sclerosis is relapsing remitting multiple sclerosis.

According to some embodiments, the method further comprises the administration of an additional therapeutic agent to said subject.

According to some embodiments, the additional therapeutic agent is administered prior to, concomitantly, or following the administration of the at least one compound, or a pharmaceutical composition comprising said at least one compound.

In compounds utilized according to the invention:

The terms "small molecule" and "small organic molecule" as used herein are interchangeable and refer to an organic molecule having molecular weight not more than 2000 gr/mol. According to some embodiments, the molecular weight of the small molecule is not more than 1000 gr/mol. According to some embodiments, the molecular weight of the small molecule is not more than 750 gr/mol. According to some embodiments, the molecular weight of the small molecule is not more than 500 gr/mol.

The term "carbocyclyl" as used herein refers to a ring structure comprising a plurality of carbon atoms and one or more heteroatom selected from N, S and O. The carbocyclyl may be a 5- or 6-membered ring comprising a single ring structure or a ring structure comprising two or more rings, each of said two or more rings may be a 5- or 6-membered ring. The two or more rings in a ring structure may fused to each other or associated to each other via a covalent bond.

The term(s) "alkyl", "alkenyl" and "alkynyl" carbon chains, if not specified, refer to carbon chains each containing from 1 to 20 carbons, or 1 or 2 to 16 carbons, and are straight or branched. Each such group may be substituted. In some embodiments, the carbon chain contains 1 to 10 carbon atoms. In some embodiments, the carbon chain contains 1 to 6 carbon atoms. In some embodiments, the carbon chain contains 2 to 6 carbon atoms. In some embodiments, the alkyl is a halogenated alkyl. The term halogenated alkyl refers to any alkyl chain covalently connected to at least one halogen atom, such as, but no limited to, trifluoromethyl. Alkenyl carbon chains may contain from 2 to 20 carbons, or 2 to 18 carbons, or 2 to 16 carbons, or 2 to 14 carbons, or 2 to 12 carbons, or 2 to 10 carbons, or 2 to 8 carbons, or 2 to 6 carbons, or 2 to 4 carbons. The alkenyl carbon chain may similarly contain 1 to 8 double bonds, or 1 to 7 double bonds, or 1 to 6 double bonds, or 1 to 5 double bonds, or 1 to 4 double bonds, or 1 to 3 double bonds, or 1 double bond, or 2 double bonds. Alkynyl carbon chains from 2 to 20 carbons, or 2 to 18 carbons, or 2 to 16 carbons, or 2 to 14 carbons, or 2 to 12, or carbons 2 to 10 carbons, or 2 to 8 carbons, or 2 to 6 carbons, or 2 to 4 carbons. The alkynyl carbon chain may similarly contain 1 to 8 triple bonds, or 1 to 7 triple bonds, or 1 to 6 triple bonds, or 1 to 5 triple bonds, or 1 to 4 triple bonds, or 1 to 3 triple bonds, or 1 triple bond, or 2 triple bonds. Exemplary alkyl, alkenyl and alkynyl groups include, but are not limited to, methyl, ethyl, propyl, isopropyl, isobutyl, n-butyl, sec-butyl, tert-butyl, isohexyl, allyl (propenyl) and propargyl (propynyl). The term "halogenated alkyl" refers to an alkyl group having at least one halogen covalently connected thereto. Exemplary halogenated alkyl groups include, but are not limited to, trifluoromethyl, chloromethyl and the like.

The group designated "—$C_1$-$C_5$-alkylene-" is an alkylene having between 1 and 5 carbon atoms. In some embodiments, the group is selected from methylene, ethylene, propylene, butylene and pentylene or any other alkyl that has between and 5 carbon atoms such as iso-propylene, and others. The group may be substituted.

The group designated "—$C_2$-$C_5$-alkenylene-" is a carbon group comprising at least two carbon atoms, and one or more C=C bonds (double bonds). The group may be substituted.

A "cycloalkyl" refers to a saturated mono- or multi-cyclic ring system, in certain embodiments of 3 to 10 carbon atoms, in other embodiments 3 to 6 carbon atoms; cycloalkenyl and cycloalkynyl refer to mono- or multicyclic ring systems that respectively include at least one double bond and at least one triple bond. Cycloalkenyl and cycloalkynyl groups may, in some embodiments, may contain between 3 to 10 carbon atoms, in further embodiments, between 4 to 7 carbon atoms and cycloalkynyl groups, in further embodiments, containing 8 to 10 carbon atoms. The ring systems of the cycloalkyl, cycloalkenyl and cycloalkynyl groups may be composed of one ring or two or more rings which may be joined together in a fused, bridged or spiro-connected fashion.

An "aryl" refers to aromatic monocyclic or multicyclic groups containing from 6 to 10 carbon atoms. Aryl groups include, but are not limited to groups such as unsubstituted or substituted fluorenyl, unsubstituted or substituted phenyl, and unsubstituted or substituted naphthyl. The group "—$C_6$-arylene-" is phenyl or a phenyl substituted group.

A "heteroaryl" refers to a monocyclic or multicyclic aromatic ring system, in certain embodiments, of about 5 to about 15 members where one or more, in some embodiments 1 to 3, of the atoms in the ring system is a heteroatom, that is, an element other than carbon, including e.g., nitrogen, oxygen or sulfur. The heteroaryl group may be optionally fused to a benzene ring. Heteroaryl groups include, but are not limited to, furyl, imidazolyl, pyrimidinyl, tetrazolyl, thienyl, pyridyl, pyrrolyl, thiazolyl, isothiazolyl, oxazolyl, isoxazolyl, triazolyl, quinolinyl and isoquinolinyl.

A "heterocyclyl" refers to a saturated mono- or multicyclic ring system, in one embodiment of 3 to 10 members, in another embodiment of 4 to 7 members, in a further embodiment of 5 to 6 members, where one or more, in certain embodiments, 1 to 3, of the atoms in the ring system is a heteroatom, that is, an element other than carbon, including but not limited to, nitrogen, oxygen or sulfur. In embodiments where the heteroatom(s) is nitrogen, the nitrogen is optionally substituted with alkyl, alkenyl, alkynyl, aryl, heteroaryl, aralkyl, heteroaralkyl, cycloalkyl, heterocyclyl, cycloalkylalkyl, heterocyclylalkyl, acyl, guanidine, or the nitrogen may be quaternized to form an ammonium group where the substituents are selected as above.

The terms "halide", "halogen" and "halo" describe fluorine, chlorine, bromine or iodine.

The term "alkoxy" refers to —O-alkyl. Thus, the alkoxy group is an alkyl (carbon and hydrogen chain) group singularly bonded to oxygen. Non limiting examples include methoxy (OMe) and ethoxy (OEt).

The groups "—O$^-$" and "O$^-$" refer to negatively charged oxygen atom. It is to be understood that the negatively charged oxygen atom is coupled with a cation, such as a metal cation, including but not limited to, Na$^+$, K$^+$, Li$^+$; or an organic cation, such as NR''''R'''R''R'$^+$, wherein R'''', R''', R'', and R' may each independently be a hydrogen atom or an alkyl group.

The term "amine" refer to the —NR'R$_2$" group. The group "—NR'R''" refers to an amine group wherein R$_1$ and R$_2$ are independently selected from hydrogen, alkyl, alkenyl, alkenyl, cycloalkyl, cycloalkenyl, cycloalkynyl, aryl, heteroaryl, heterocyclyl, ester and carbonyl, each as defined herein or alternatively known in the art.

As used herein, the term "salt" or "a salt thereof" refers to pharmaceutically acceptable salts of the compounds disclosed herein. Not limiting examples includes acid addition cationic salts and anionic salts. "Acid addition cationic salts" are typically formed when a compound having a basic atom is exposed to an acidic environment. These include, as a non-limiting examples, ammonium ions, such as those form by protonation of a nitrogen-containing compound. "anionic salt" are typically formed when a compound having a hydrogen atom is exposed to a basic environment. These include, as a non-limiting examples, carboxylates, which may be formed upon deprotonation of a carboxylic acid or saponification of ester; and compounds having a deprotonated nitrogen atom.

When referring to a possible substitution, any one groups recited to be "optionally substituted" or otherwise "substituted" is said to have one or more atoms or group of atoms substituting a native atom or group (such as a hydrogen atom) on any of the atoms thereof. In some embodiments, the substituent is selected from alkyl, alkenyl, alkynyl, cycloalkyl, cycloalkenyl, cycloalkynyl, aryl, heteroaryl, heterocyclyl, halogen, alkylene-COOH, ester, —OH, —SH, and —NH. In some embodiments, the number of substituents on a certain ligand is 0 or 1 or 2 or 3 or 4 or 5 or 6 or 7 or 8 or 9 or 20 substituents.

The invention further provides use of any of the compounds herein designated SM1, SM6, SM7 or SM9.

The present invention further provides compositions, e.g., pharmaceutical compositions comprising at least one compound of Formula (I), e.g., compounds herein designated "SM1" or "SM9" and optionally a pharmaceutically acceptable carrier, diluent or excipient.

By another aspect, the present invention provides pharmaceutical compositions comprising at least one compound designated "SM1", "SM6", "SM7" or "SM9" and optionally a pharmaceutically acceptable carrier, diluent or excipient for use in the treatment of neuroinflammatory disorders, e.g. multiple sclerosis, neurotoxicity or brain damage.

The invention also encompasses enantiomers, stereoisomers, or any other isomers of any of the herein recited compounds.

The therapeutic efficacy of the compounds of the invention or any of their enantiomers, stereoisomers, or isomers can be tested in vitro or in animal models, for example the EAE animal model.

All of these compounds are available from commercial sources, e.g. Thermo Fisher Scientific Inc.

The compounds of the invention may be modified and administered as prodrugs.

As used herein, the term "pharmaceutical composition" refers to a preparation of at least one organic small molecule as described herein. In addition, the pharmaceutical compositions of the invention comprise a pharmaceutically acceptable carrier, diluent or excipient.

The term "pharmaceutically acceptable carrier, diluent or excipient" includes any and all solvents, dispersion media, coatings, antibacterial and antifungal agents and the like and refers to a carrier or a diluent that does not cause significant irritation to an organism and does not abrogate the biological activity and properties of the administered small organic compound. An adjuvant is included under this term. Herein, the term "excipient" refers to an inert substance added to a pharmaceutical composition to further facilitate administration of an active ingredient.

Examples, without limitation, of excipients or non-toxic carriers include but are not limited to calcium carbonate, calcium phosphate, various sugars and types of starch, glucose, sucrose, sodium saccharin, mannitol, lactose, cellulose derivatives, gelatin, vegetable oils, magnesium stearate, magnesium carbonate, talcum, polyalkylene glycols, and polyethylene glycols.

Pharmaceutical compositions according to the invention may be manufactured by processes well known in the art, using one or more pharmaceutically acceptable carriers, e.g., by means of conventional mixing, dissolving, granulating, emulsifying, encapsulating, entrapping, or lyophilizing processes. Proper formulation is dependent upon the route of administration chosen. The pharmaceutical composition may be produced as solid dosage form, e.g. a powder, pill, tablet or the like, or as a solution, emulsion, suspension, aerosol, syrup or elixir.

The term "treatment" or "method of treating" as herein defined refers to preventing recurrence of a disease, reduction or alleviation of symptoms of the disease, decreasing the rate of disease progression, amelioration or reduction of the disease severity or state and improved prognosis.

In some embodiments the effect of the treatment according to the invention on subjects suffering from MS may be monitored by the "Expanded Disability Status Scale" (EDSS), which is a scale that ranges from 0 to 10 in 0.5 unit increments that represent levels of disability. Scoring is based on an examination by a neurologist. EDSS steps 1.0 to 4.5 refer to people with MS who are able to walk without any aid and is based on measures of impairment in eight functional systems (FS), as follows: pyramidal, cerebellar, brain stem, sensory, bowel & bladder, visual, cerebral, and other (ambulation) [15]. Each functional system is scored on a scale of 0 (normal) to 5 or 6 (maximal impairment). EDSS steps 5.0 to 9.5 are defined by the impairment to walking.

The terms "neuroinflammatory disorder", "neuroinflammatory disease" or "neuroinflammatory condition" are used interchangeably herein and refer to conditions where immune responses damage components of the nervous system. Common examples are multiple sclerosis (MS) and neuromyelitis optica (NMO) which are characterized by inflammatory demyelination of the central nervous system and subsequent damage to nerve cells and axons. Inflammatory mechanisms have also been implicated in the pathogenesis of many other CNS disorders including systemic inflammatory conditions with central nervous system involvements such as vasculitis, sarcoidosis, and Behcet disease, as well as neurodegenerative, psychiatric disorders, neurotoxic conditions, stroke and brain injury.

The term "neurodegenerative disease, condition or disorder" as herein defined is the progressive loss of structure or function of neurons, including death of neurons, in the brain or spinal cord. Neurodegeneration is observed after viral insult and mostly in various so-called 'neurodegenerative diseases', generally observed in the elderly, such as Alzheimer's disease (AD), Parkinson's disease (PD), and Amyotrophic Lateral Sclerosis (ALS, also termed Lou Gehrig's disease).

In some specific embodiments the pharmaceutical composition according the invention is for the treatment of a "demyelinating disease". The term "demyelinating disease" as herein defined is any disease of the nervous system in which the myelin sheath of neurons is damaged or removed resulting in abrogated function of the neuronal cells.

In some embodiments, the neurodegenerative disease according to the invention is multiple sclerosis. In further specific embodiments the pharmaceutical composition according to the invention is for the treatment of multiple sclerosis.

The term "Multiple Sclerosis" (MS) as herein defined is a chronic inflammatory neurodegenerative disease of the central nervous system that destroys myelin, oligodendrocytes and axons. MS is the most common neurological disease among young adults, typically appearing between the ages of 20 and 40. The symptoms of MS vary, from the appearance of visual disturbance such as visual loss in one eye, double vision to muscle weakness fatigue, pain, numbness, stiffness and unsteadiness, loss of coordination and other symptoms such as tremors, dizziness, slurred speech, trouble swallowing, and emotional disturbances. As the disease progresses patients may lose their ambulation capabilities, may encounter cognitive decline, loss of self-managing of everyday activities and may become severely disabled and dependent.

MS symptoms develop because immune system elements attack the brain's cells (glia and/or neurons) and damage the protective myelin sheath of axons. The areas in which these attacks occur are called lesions that disrupt the transmission of messages through the brain.

Multiple sclerosis is classified into four types, characterized by disease progression: (1) Relapsing-remitting MS (RRMS), which is characterized by relapses (attacks of symptom flare-ups) followed by remissions (periods of stabilization and possible recovery; while in some remissions there is full recovery, in other remissions there is partial or no recovery). Symptoms of RRMS may vary from mild to severe, and relapses may last for days or months. More than 80 percent of people who have MS begin with relapsing-remitting cycles; (2) Secondary-progressive MS (SPMS) develops in people who have relapsing-remitting MS. In SPMS, relapses may occur, but there is no remission (stabilization) for a meaningful period of time and the disability progressively worsens; (3) Primary-progressive MS (PPMS), which progresses slowly and steadily from its onset and accounts for less than 20 percent of MS cases. There are no periods of remission, and symptoms generally do not decrease in intensity; and (4) Progressive-relapsing MS (PRMS). In this type of MS, people experience both steadily worsening symptoms and attacks during periods of remission.

Currently, multiple sclerosis has no cure. Treatment usually focuses on strategies to treat MS attacks, manage symptoms and reduce the progress of the disease. Among the known agents used for the treatment of MS are corticosteroids that are mainly used to reduce the inflammation that spikes during a relapse, beta interferons, which slow the progress of multiple sclerosis, reduce the number of attacks and lessen the severity of attacks, Glatiramer acetate (Copaxone®), which reduces the number of MS attacks, Fingolimod (Gilenya®), Natalizumab (Tysabri®) and other agents known in the art. New emerging therapies that reduce the relapse rate and mildly affect disability progress include dimethyl fumarate (BG-12, Tecfidera®), teriflunomide (Aubagio®), Alemtuzumab (Campath® 1-H, Lemtrada®) and Ocrelizumab (Ocrevus™).

Diagnosis of multiple sclerosis may be performed by any method known in the art and includes lumbar puncture (spinal tap) for cerebrospinal fluid tests, including CSF oligoclonal banding, MRI scan of the brain and MRI scan of the spine (spinal cord) and neuronal pathway function study (evoked potential tests).

As shown in the Examples below (e.g. Examples 2 and 3), intraperitoneal administration of the small organic compounds of the invention SM1, SM7 and SM9 ameliorated the clinical symptoms in a relapsing/remitting experimental autoimmune encephalomyelitis (RR-EAE) animal model, a well-established model mimicking multiple sclerosis (MS).

The term "Experimental autoimmune encephalomyelitis" (EAE, or Experimental Allergic Encephalomyelitis) as herein defined generally refers to an induced inflammatory demyelinating disease of the central nervous system (CNS) which is widely accepted as an animal model of human CNS demyelinating diseases, including, but not limited to, multiple sclerosis (MS) and acute disseminated encephalomyelitis (ADEM).

EAE can be induced in a number of species, including mice, rats, guinea pigs, rabbits and primates. Disease induction is usually done by exposure of the animals to various antigens. The most commonly used antigens are spinal cord homogenate (SCH), purified myelin, myelin protein such as myelin basic protein (MBP), myelin proteolipid protein (PLP or lipophilin), and myelin oligodendrocyte glycoprotein (MOG), or peptides of these proteins, all resulting in distinct models with different disease characteristics regarding both immunology and pathology.

Depending on the antigen used and the genetic make-up of the animal, rodents can display a monophasic bout of EAE, a relapsing-remitting form, or chronic EAE. The typical susceptible rodent will debut with clinical symptoms around two weeks after immunization and will present symptoms of a relapsing-remitting disease.

Modeling of multiple sclerosis may be performed with SJL/J Mice. This EAE model is induced in 8-week old SJL/J female mice by the proteolipid protein (PLP) fragment (along with Pertussis toxin). This model exhibits a relapsing-remitting (RR) disease course, resembling those observed in MS patients.

Modeling of multiple sclerosis may also be performed using C57BL/6 female mice, in which disease is induced with myelin-oligodendrocyte glycoprotein peptide (MOG). This model represents progressive (also referred to as chronic) form of the disease.

As known in the art, model animals are usually scored for disease activity (termed "Disease Activity Index", DAI) using the following scoring index: "0", Normal mouse, no overt signs of disease, "1", Limp tail or hind limb weakness but not both, "2", Limp tail and hind limb weakness, "3", Partial hind limb paralysis, "4" Complete hind limb paralysis, and "5", Death or sacrifice for humane reasons. There are also other DAI, for example DIA that use the following scoring: "1", tail atony; "2", mild to moderate hind limb weakness; "3", severe hind limb weakness; "4", complete paralysis of one or more limbs; "5", moribund.

The above scoring index may thus be used for monitoring the severity of the disease and the onset of relapses in order to determine the therapeutic effect of the small organic molecules of the invention.

Therefore, in one embodiment, the compounds of the invention can be used for the treatment of RR-MS.

In other embodiments, the compounds of the invention can be used for the treatment of secondary-progressive MS (SPMS), or primary-progressive MS (PPMS), or progressive-relapsing MS (PRMS).

In another aspect, the present invention provides a method of treating a multiple sclerosis, the method comprising the step of administering to a subject in need thereof a therapeutically effective amount of at least one compound of a formula selected from the group consisting of: "SM1", "SM6" "SM7" and "SM9", or a pharmaceutical composition comprising said at least one compound.

By way of example, the step of administering a compound of the invention or a pharmaceutical composition of the invention may be performed by, but is not limited to, the following routes of administration: oral, rectal, transmucosal, transnasal, intestinal, or parenteral delivery, including intramuscular, subcutaneous, and intramedullary injections, as well as intrathecal, direct intraventricular, intravenous, intraperitoneal, intranasal, or intraocular injections. Alternately, one may administer the pharmaceutical composition according to the invention in a local rather than systemic manner, for example, via injection of the pharmaceutical composition directly into a tissue region of a subject, e.g. into the affected CNS areas.

In some embodiments, the small organic molecule of the invention is administered in combination with an additional therapeutic agent.

The additional therapeutic agent may be any therapeutic agent suitable or known for treating multiple sclerosis or for reducing the relapse rate and affecting disability progress. Non-limiting examples include Interferon-beta1 (such as Avonex®, Betaferon®, Rebif®), Glatiramer acetate (Copaxone®), Fingolimod (Gilenya®), Natalizumab (Tysabri®), Ocrelizumab (Ocrevus®) and other agents known in the art.

The additional therapeutic agent may be a cellular therapy including administration of cells including but not limited to mesenchymal stem cells (MSC), MSC-like cells, neural progenitor cells, $CD34^+$ cells, $CD133^+$ cells from all available sources, induced pluripotent stem cells (iPSC), differentiated pluripotent stem cells, and the like.

In one embodiment, said additional therapeutic agent is an agent which mediates opening of the BBB, for example Mannitol, which may be intravenously injected.

The additional therapeutic agent may be formulated together with the small organic compound of the invention, or be part of a separate composition. The additional agent may be administered together with the compounds of the invention or separately. It may be administered prior to, concomitantly or following the administration of the compounds or pharmaceutical compositions of the invention.

As known in the art, the term the "blood-brain barrier (BBB)" relates to the structural membrane separation of the central nervous system from circulating blood.

The term "therapeutically effective amount" (or amounts) of the at least one small organic molecule according to the invention is determined by such considerations as are known in the art in order to cure, arrest or at least alleviate the medical condition. The precise dose and frequency of administration depends on the severity of the patient's disease, on the route of administration, and on the pharmacokinetics of the compound. Determining the dose is a routine procedure and well known to physicians and other of ordinary skill in the art. For any preparation used in the methods of the invention, the dosage or the therapeutically effective amount can be estimated initially from in vitro assays, cell culture assays, and in vivo experiments performed in animal models, e.g. EAE.

For example, the dosage provided below was estimated based on the EAE mouse model of multiple sclerosis. As shown in Examples 2 and 3 below, treatment with 10 mg/kg or 20 mg/kg of each of SM1, SM7 or SM9 ameliorated EAE. Remarkably, the symptoms in the treated EAE mice were less severe than those in the controls, at each phase of the study. This effect was also manifested by the fact that in the treated EAE mice group, fewer mice exhibited a more severe form of the disease (i.e. clinical score of 2-5). In addition, it was shown that the treatment lead to increasing amount of myelin in spinal cord of EAE mice indicating increased remyelination processes or decreased demyelination in response to these SMs treatment, or both.

Non-limiting examples of therapeutic dosages include but are not limited to 400-800 mg per about 70 kg human.

It is to be noted that the amount of the small organic molecule to be administered may vary by about 5-25%, in consideration of the molecular weight and other features of a specific agent. Thus the term "about" as herein defined refers to a fluctuation of 5-25% of the amount as herein defined. Preferably, the term "about" encompasses variations of +/−10%, more preferably +/−5%, even more preferably +/−1%, and still more preferably +/−0.1% from a specified value.

The small organic molecule according to the invention or any pharmaceutical composition comprising same may be administered to a patient at a single or at multiple administrations. The small organic molecule or the pharmaceutical composition comprising same may be administered to the patient continuously or for discrete periods of time, as determined by such considerations as known to a person skilled in the art in order to cure, arrest or at least alleviate the medical condition.

Toxicity and therapeutic efficacy of the small organic molecule described herein can be determined by standard pharmaceutical procedures in vitro, in cell cultures or experimental animals. The data obtained from these in vitro and cell culture assays and animal studies can be used in formulating a range of dosages for use in human. The dosage may vary depending upon the dosage form employed and the route of administration.

The term "subject" as used herein means warm-blooded animals, such as for example rats, mice, dogs, cats, guinea pigs, primates and humans. Although the methods of the invention are particularly intended for the treatment of a human subject suffering from a neurodegenerative disease, other mammalian subjects are included. The terms subject and patient are used interchangeably herein.

The present invention also discloses a compound of the formula "SM1", "SM6", "SM7" or "SM9" and a pharmaceutically acceptable carrier, excipient or diluent for use in a method of treatment of a subject suffering from multiple sclerosis, wherein said method comprising administering said at least one small organic molecule and a pharmaceutically acceptable carrier to said subject.

Further disclosed is use of at least one compound of the formula "SM1", "SM6", "SM7" or "SM9" and a pharmaceutically acceptable carrier in the preparation of a pharmaceutical composition for the treatment of a subject suffering from multiple sclerosis.

The compounds of the invention were initially selected based on their ability to inhibit BMP-2 signaling in vitro. As shown in Example 1, the small organic molecules SM1, SM6, SM7 and SM9, were screened out of a large library for their ability to inhibit BMP-2 in vitro without leading to cytotoxicity in mouse ATDC5 cells. In addition, as shown in Examples 4, 7 and 8, these compounds showed an increase in several markers that are indicative of neural differentiation in vitro.

The term "bone morphogenetic protein (or proteins)" (BMPs) as herein defined refers to a group of growth factors also known as cytokines or metabologens. BMPs induce the formation of bone and cartilage, and have multiple roles in embryonic brain development. Twenty BMPs have been discovered to date, of these, six BMPs (i.e. BMP-2 through BMP-7) belong to the Transforming growth factor 3 (beta) super family of proteins. In particular, the present invention concerns BMPs that are associated with neuronal proliferation and development. Non-limiting examples include BMP-2 and BMP-4. In a specific embodiment the BMP is human BMP.

"Bone morphogenetic protein 2" (or BMP-2), as other bone morphogenetic proteins, BMP-2 plays an important role in the development of bone and cartilage. It is involved in the hedgehog pathway, TGF β signaling pathway, and in cytokine-cytokine receptor interaction. It is involved also in cardiac cell differentiation and epithelial to mesenchymal transition. BMP-2 acts as a disulfide-linked homodimer and was shown to stimulate the production of bone.

In some embodiments, the Bone morphogenetic protein 2 according to the invention is human BMP-2, having the NCBI (National Center for Biotechnology Information) accession number NM_001200.2.

"Bone morphogenetic protein 4" (or BMP-4), is also involved in bone and cartilage development, specifically tooth and limb development and fracture repair. This particular family member plays an important role in the onset of endochondral bone formation in humans. It has been shown to be involved in muscle development, bone mineralization, and ureteric bud development. In human embryonic development, BMP-4 is a critical signaling molecule required for the early differentiation of the embryo and establishing of a dorsal-ventral axis. BMP-4 is secreted from the dorsal portion of the notochord, and it acts in concert with sonic hedgehog (released from the ventral portion of the notochord) to establish a dorsal-ventral axis for the differentiation of later structures.

In some embodiments, the Bone morphogenetic protein 4 according to the invention is human BMP-4, having the NCBI (National Center for Biotechnology Information) accession number P12644.

BMPs interact with specific receptors on the cell surface, referred to as bone morphogenetic protein receptors (BMPRs). Signal transduction through BMPRs results in mobilization of members of the SMAD family of proteins. As used herein the term "BMP signaling" refers to the signaling pathway initiated by binding of a BMP to its receptor and the subsequent cellular processes induced by this binding, e.g., mobilization of members of the SMAD family of proteins.

It is to be understood that this invention is not limited to the particular examples, process steps, and materials disclosed herein as such process steps and materials may vary somewhat. It is also to be understood that the terminology used herein is used for the purpose of describing particular embodiments only and not intended to be limiting since the scope of the present invention will be limited only by the appended claims and equivalents thereof.

It must be noted that, as used in this specification and the appended claims, the singular forms "a", "an" and "the" include plural referents unless the content clearly dictates otherwise.

Unless defined otherwise, all technical and scientific terms used herein have the same meaning as commonly understood by one of ordinary skill in the art to which this invention is related. The following terms are defined for purposes of the invention as described herein.

EXAMPLES

Without further elaboration, it is believed that one skilled in the art can, using the preceding description, utilize the present invention to its fullest extent. The following preferred specific embodiments are, therefore, to be construed as merely illustrative, and not limitative of the claimed invention in any way.

Standard molecular biology protocols known in the art not specifically described herein are generally followed essentially as in Sambrook & Russell, 2001.

Abbreviations

Small molecules—SM
Experimental autoimmune encephalomyelitis—EAE;
Relapsing and remitting—RR;
Multiple sclerosis—MS;
Relapsing and remitting experimental autoimmune encephalomyelitis—RR—EAE;
Proteolipid protein peptide—PLP;
Myelin-oligodendrocyte glycoprotein peptide—MOG;
Phosphate buffered saline—PBS;
Complete Freund's Adjuvant—CFA;
Pertussis toxin—PTX;
Bone Morphogenetic Protein—BMP;
Blood brain barrier—BBB;
Central nervous system—CNS;
Hour—hr, h;
Minute—min.
Experimental Procedures
High Throughput Screening (HTS) Bioassay
Poly-L-lysine (Sigma-Aldrich) was added to 384-well plates and was removed after 30 min of incubation at RT. An assay medium containing DMEM/F12, 2% FBS, 100 units/ml penicillin, 100 mg/ml streptomycin (Biological industries) was added to each well. Recombinant human BMP-2 (rhBMP-2, R&D Systems) was then added to each well to a final concentration of 2 µg/ml. ATDC5 cells (Sigma-Aldrich) were harvested, re-suspended in assay medium and added to a final concentration of 2000 cells/well. Finally, heparin (Sigma-Aldrich) was added to a final concentration of 2 µg/ml. The cells were incubated for 48 hours at 37° C. with 5% $CO_2$ in a humidified chamber in the presence or absence of potential small molecule inhibitors of BPM-2. After incubation, ALP levels and cell viability were determined using a completely automated protocol. Cells were washed with PBS, lysed using a lysis buffer containing 0.2% Triton X-100 in PBS supplemented with a protease inhibitor cocktail (Sigma-Aldrich) and incubated for 25 min at RT. ALP level was then determined by addition of CDP-Star® chemiluminescent substrate (Sigma-Aldrich) and measurement of luminescence after incubation for 25 min at RT in the dark. Cell viability was finally determined by addition of CellTiter-Glo® reagent (Biological Industries) and luminescence measurement after 10 min of incubation.

Experimental Autoimmune Encephalomyelitis (EAE) Induction in Mice

RR-EAE was induced in SJL female mice (6-8 week old) by subcutaneous immunization (day 0) with 100 μg/mouse proteolipid protein peptide (PLP$_{139-151}$, synthesized by Sigma-Aldrich) in 0.1 ml PBS. The peptide was emulsified in an equal volume of Complete Freund's Adjuvant (CFA, from DIFCO) containing 500 μg *Mycobacterium tuberculosis* H$_{37}$RA (MT, from DIFCO). The mice also received an intraperitoneal injection of 300 ng pertussis toxin (PTX, from Sigma-Aldrich) in 0.2 ml PBS. A second injection of PTX (300 ng/mouse) was given 48 h later.

Mice were monitored for symptoms of RR-EAE and were scored as follows: "0" for no disease; "1", tail paralysis; "2", hind limb weakness; "3", hind limb paralysis; "4", hind limb and forelimb weakness/paralysis; "5", moribund.

All procedures involving mice were performed according to the guidelines of the Animal Ethical Committee of the Sourasky Medical Center.

In Vitro Differentiation Assay of P19 Cells

P19 cells were grown in a-minimum essential medium (aMEM) (Gibco) containing 7.5% calf serum, 2.5% fetal calf serum, and 0.4 μl/ml penicillin-streptomycin (Gibco), at 37° C., 5% CO2. Cells were replenished with fresh medium every 48 h. For the differentiation study, P19 cells were cultured at concentration of 2×10$^5$ cells/60 mm bacterial dish and were either unstimulated or incubated with the following stimulations:

1) 5×10$^{-7}$ M all-trans-retinoic acid (RA) (Sigma)
2) RA+5 ng/ml rhBMP2 (R&D systems)
3) RA+rhBMP-2+500 ng/ml mouse anti-human BMP-2/4 mAb (R&D systems)
4) RA+rhBMP-2+SM1/SM7/SM9 (Maybridge (Hit-Finder™ Collection)) at concentrations: 0.625, 1.25 and 2.5 M.

The medium, including RA, BMP supplements and SMs, was replenished after 48 h. After 4 days, aggregates which formed during RA treatment were dispersed enzymatically (0.05% v/v trypsin-0.02% v/v EDTA) and mechanically and plated in tissue culture grade dishes. At this stage, cells were cultured in RA-, BMP- and SM-free medium, which was refreshed every 48 h. MAP-2 positive neurons were examined at day 8 (i.e., day 4 post-RA treatment) by immunofluorescence. Briefly, at day 7, cells were re-cultured in 24 well-plates with cover slips at a final concentration of 5×10$^4$ cells/well. On day 8, cells were washed with PBS, fixed with PFA 4% for 15 min, permeabilized with 0.5% Triton Tx, blocked with 10% FCS, 0.1% BSA and 0.05% Tween for 30 min, and stained with MAP2 rabbit mAb (1:100, D5G1, Cell Signaling) for 1 hr. The second antibody step was performed by labeling with Alexa Fluor® 488-conjugated IgG antibody to rabbit for 1 h (1:1000; Molecular Probes USA).

Determination of SMAD1/5/8 Signaling by Western Blot Analysis

P19 cells were seeded in 6-well-plates (3.5×10$^5$ cells/well). On the following day, the cells were either untreated or treated with 5×10$^{-7}$ M RA, 5 ng/ml BMP-2 or SMs for 4 h. Cells were washed with ice cold PBS, harvested and lysed with ice cold RIPA buffer (Sigma-Aldrich) supplemented with protease inhibitor cocktail and sodium orthovanadate (Na3VO4) as phosphatase inhibitor (Sigma-Aldrich). Protein concentrations were determined using a BCA protein assay kit (Pierce, Rockford, Ill.). Cell lysates (40-60 μg protein) were separated by 4-15% SDS-PAGE gel electrophoresis and then transferred to nitrocellulose membranes at 0.2 A for 2 h. The membranes were blocked at room temperature for 1 h in 5% (w/v) non-fat-dried milk and then incubated with anti-phospho-Smad1/5/9, anti-Smad1 (Cell signaling Technology, Beverly, Mass., USA) and anti-tubulin (Sigma-Aldrich) antibodies at room temperature for 2 h. The membranes were washed and incubated with alkaline phosphatase-conjugated secondary antibody (Jackson Laboratories Immune Research, PA, USA). Signal was detected using enhanced chemiluminescence kit (Clarity, Bio-Rad Laboratories, Richmond, Calif.) and digital images were captured by MicroChemi (DNR Bio-imaging Systems, Jerusalem, Israel). Protein levels were quantified using ImageJ software and normalized to {alpha}-tubulin.

Example 1

High Throughput Screening of Small Molecules

An ATDC5 cell based assay for assessing structure-function relationship of BMP-2 and BMP receptor IA was originally described in Keller et al (Nature Structural & Molecular Biology 2004 11, 481-488). In order to screen a large volume of potential therapeutic agents the ATDC5 cell based bioassay for detecting BMP inhibition was adapted for use in high throughput screening. The bioassay is based on the stimulation of alkaline phosphatase (ALP) production in mouse ATDC5 cells by administration of BMP-2 and heparin, and measurement of ALP levels in the presence of the potential inhibitors. The assay was characterized by the following features:

(a) optimal conditions for HTS automated instruments were found so as to obtain a satisfying gap (i.e. positive Z-prime, above 0.5) between ALP production in the presence of BMP-2, to ALP production in the absence of BMP-2 (no stimulation).

(b) a sensitive method was designed for ALP determination for HTS: namely, the use of CDP-Star® chemiluminescent substrate and luminescence measurement.

(c) both ALP production and cells' viability were measured simultaneously. This was achieved by using CellTiter-Glo® Luminescent Cell Viability Assay for assessing the cells' viability after the luminescent signal by CDP-Star® has faded. The simultaneous assessment of both ALP production and cells' viability was necessary since potentially toxic tested small molecules may lead to reduced ALP levels by cellular cytotoxicity rather than by interference with BMP-2 signaling. It was therefore essential to examine in the same cell culture both ALP levels and the cells' viability in order to exclude molecules that simply caused cell death. Particulars of the bioassay are detailed in the Experimental procedures section above.

Figure 1B:
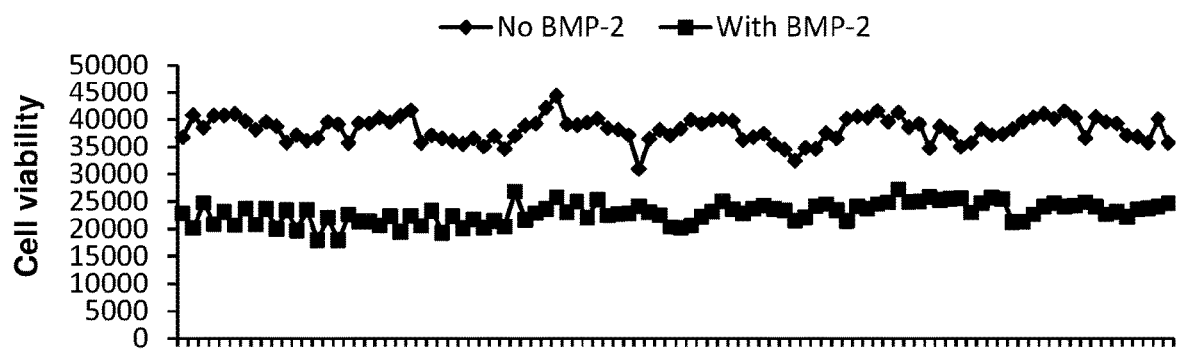
Figure 1C:
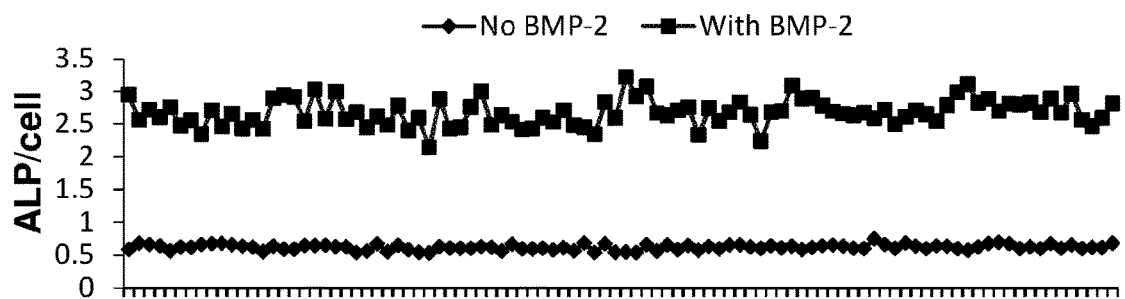
Figure 2:
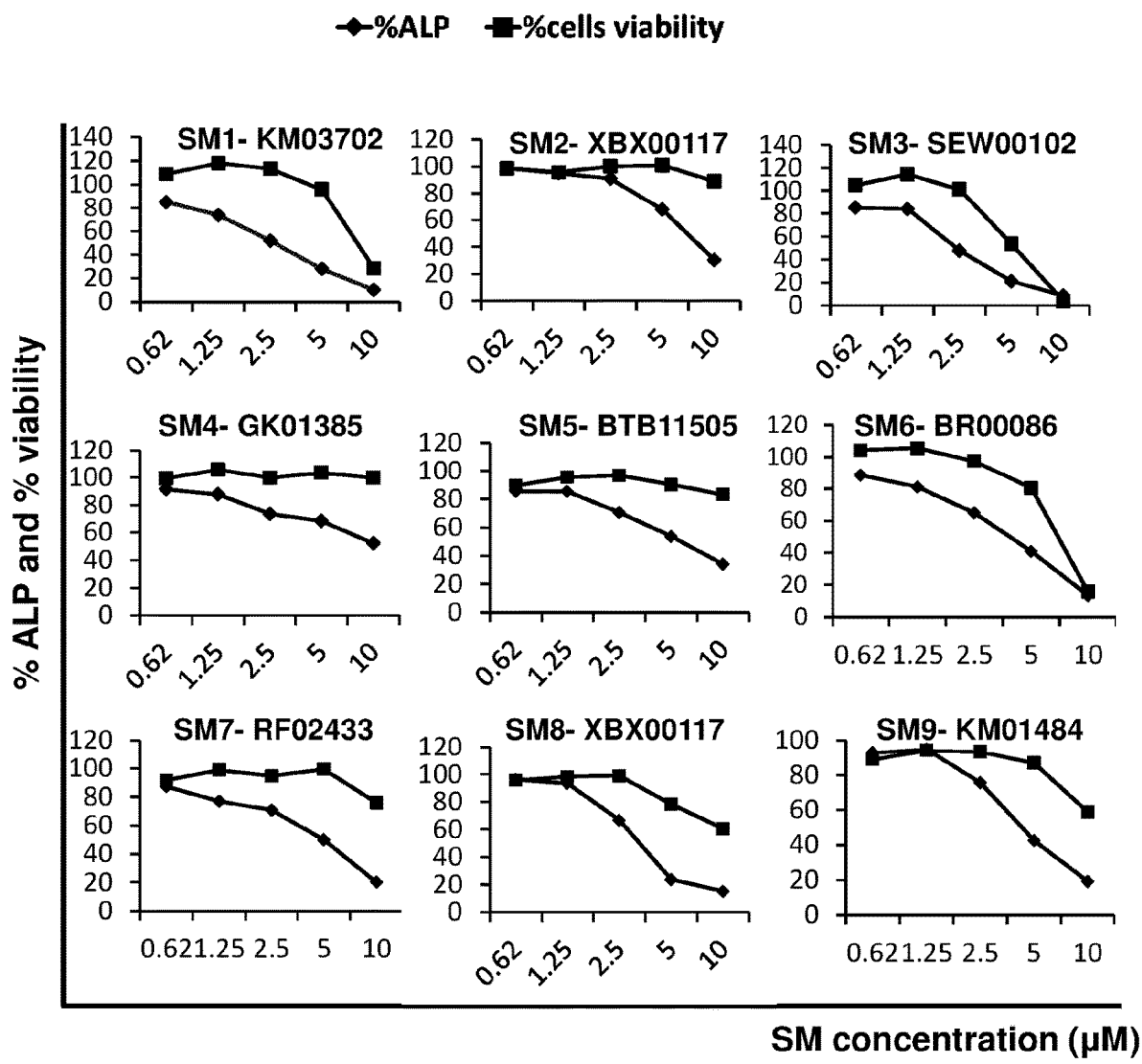
FIG. 2—The effect of SM1-SM9 on ALP stimulation by BPM-2 and on cell viability. Percent (%) ALP (diamonds) and percent (%) cell viability (squares) for SM1-SM9 are shown for various concentrations of the molecules (0.62 µM, 1.25 µM, 2.5 µM, 5 µM and 10 µM).

The efficacy of this fully automated test is demonstrated in FIG. 1. FIG. 1(A) shows ALP activity in ATDC5 cells in response to stimulation with rhBMP-2 in the presence of heparin. The ALP activity was determined by using CDP-Star® chemiluminescent substrate. Evidently, as shown in FIG. 1(B) stimulation of the cells with rhBMP-2 reduces cell number. This may be a result of BMP-2-induced chondrogenesis of ATDC5 cells, followed by reduced proliferation. As shown in FIG. 1(C) the ratio of ALP/cell was 4.3-fold induced, Z'=0.59. Z' is a parameter indicating the significance of the effect, namely how high is the ALP signal in the presence of BMP2 as compared to the level of the signal in the absence of BMP2. The closer Z' is to 1 the difference is higher. The calculation is performed as follows:

$$Z'=1-3(\sigma_p\sigma_n)/|\mu_p+\mu_n|$$

whereby σ=standard deviation, μ=average, p=positive (with BMP), n=negative (without BMP) and I=value A library of small molecules (SM) was screened using the High Throughput Screening bioassay described above. About 7600 SMs were screened, from the Maybridge library, which consists of organic "drug-like" compounds, using the pre-plated HitFinder™ Collection. The compounds were added to each well to a final concentration of 5 μM, after the coating with poly-L-lysine step and before the addition of rhBMP-2. After a first screening, 96 potential molecules were selected for inhibition of BMP-2 (termed herein "hits"), which exhibit a percentage of inhibition of BMP-2 signaling higher than 25% and a percentage of cell toxicity lower than 20%. Various concentrations (0.62 μM, 1.25 μM, 2.5 μM, 5 M and 10 M) of these molecules were further tested in the bioassay to calculate the $IC_{50}$. After $IC_{50}$ determination, 17 positive hits were obtained. Nine molecules which exhibited the best $IC_{50}$ values were selected for further analysis. These molecules are termed herein SM1-SM9. The inhibitory activity of SM1-SM9 and their cytotoxic effect on the cell line are shown in FIG. 2. The ALP levels and cell viability are shown in FIG. 2 as a percentage of the ALP or viability luminescence levels in the presence of BMP-2 without the SM. The SM were tested at various concentrations, i.e. at 0.62 μM, 1.25 μM, 2.5 μM, 5 μM and 10 M.

Table 1 summarizes the chemical name, structure and IC50 values for SM1-SM9.

TABLE 1

| SM number | Maybridge Number | Chemical Name | IC 50 (μM) |
|---|---|---|---|
| SM1 | KM03702 | Methyl 3-[(2E)-2-[cyano(thiophen-2-ylsulfonyl)methylidene]hydrazinyl]-thiophene-2-carboxylate | 2.6 |
| SM2 | XBX00117 | 1,4-Dihydro-3,6-diphenyl-1,2,4,5-tetrazine | 8.5 |
| SM3 | SEW00102 | Ethyl 2-(methylthio)-4-[[[(5-nitro-2-furyl)carbonyl]amino]-1-(2-thienlmethyl)-1H-imidazole-5-carboxylate | 2.6 |
| SM4 | GK01385 | 4-(5-nitro-1,3-dioxobenzo(de)isoquinolin-2-yl)-N-[4-(trifluoromethyl)-phenyl]benzenesulfonamide | 10 |
| SM5 | BTB11505 | N1-acetyl-2-([3-(acetylamino)-3-oxopropyl]thio)benzamide | 3.8 |
| SM6 | BR00086 | N2-[3-(trifluoromethyl)phenyl)-5-nitro-2-furamide | 9.7 |
| SM7 | RF02433 | 3-hydroxy-5-[2-(trifluoromethyl)aniline]isothiazole-4-carbonitrile | 2.2 |
| SM8 | SPB07118 | 1-tert-butyl-3-[E-1-(4-(3,5-dichloro-pyridin-4-yl)oxyphenyl]ethylidene-amino)-thiourea | 2.8 |
| SM9 | KM01484 | 5-(4-chlorophenyl)-3-methylsulfonyl-1,2-oxazole-4-carbonitrile | 4.4 |

Example 2

Effect of the SMs In Vivo on Disease Progression Using RR-EAE Model

The effect of the small molecule inhibitors that were identified in Example 1 above was further tested in vivo using the experimental autoimmune encephalomyelitis (EAE) model in SJL mice. EAE serves as a model for Relapsing/Remitting multiple sclerosis (MS). EAE was induced as described in the experimental procedures section. SMs 1-9 or vehicle alone (5% DMSO in PBS) were daily administered by intraperitoneal injections of 250 pig/mouse (10 mg/kg/day), starting from day 9 post immunization, for the next 30 days. The animals were monitored until day 45 post-induction for symptoms of EAE and scored as follows: 0=no disease, 1=tail paralysis, 2=hind limb weakness, 3=hind limb paralysis, 4=hind limb plus forelimb paralysis, and 5=moribund.

Figure 3:
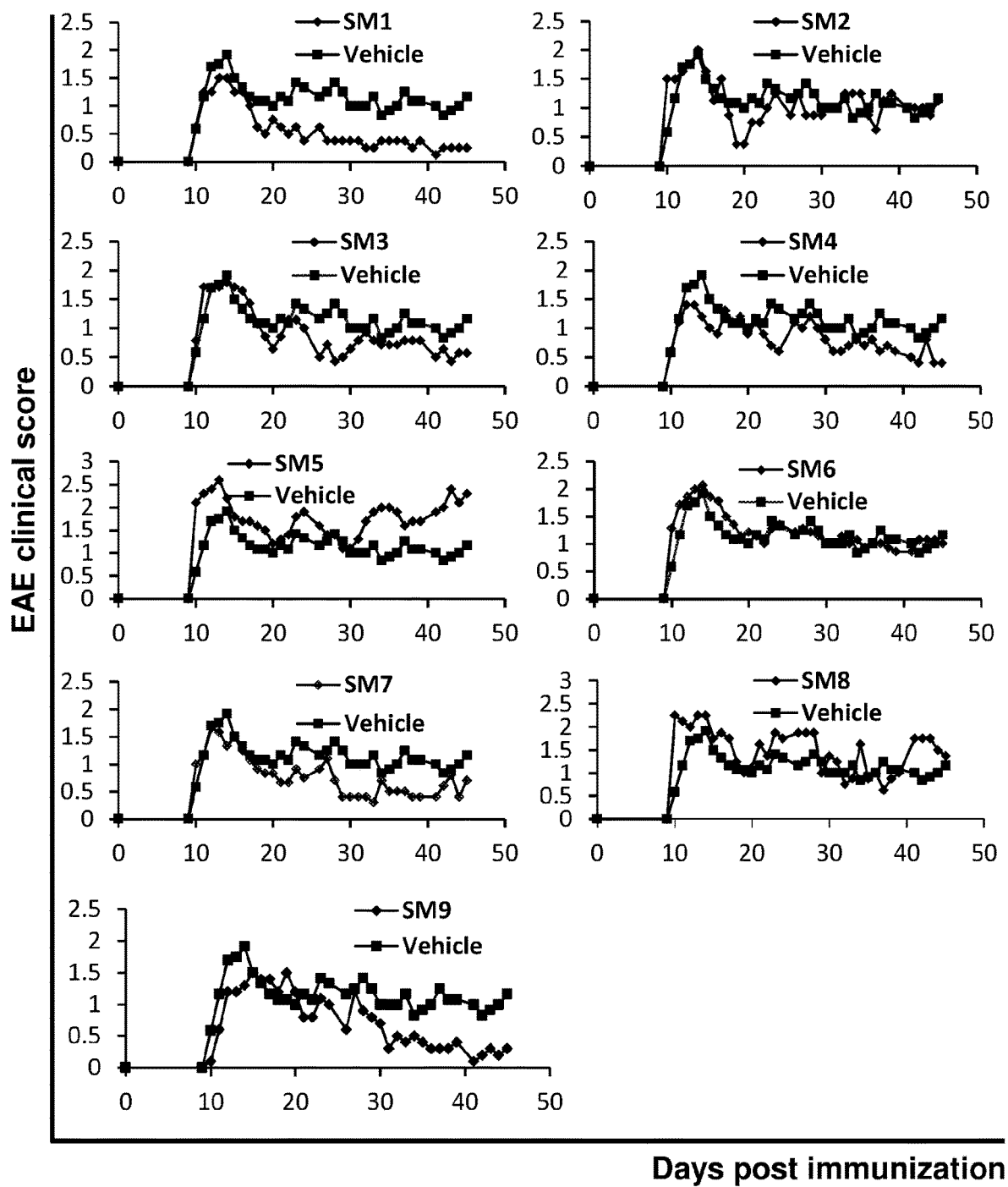
FIG. 3—The effect of SM1-SM9 in RR-EAE. EAE clinical score in RR-EAE mice, each group (n=7) treated with a small molecule (SM 1-9 respectively, 10 mg/kg/day) as compared with vehicle alone (5% DMSO in PBS, 200 µg/mouse) for 30 days from day 9 post immunization. SMs—diamonds, Vehicle—squares.

As demonstrated in FIG. 3, a beneficial effect was observed for treatment with the molecules SM1, SM7 and SM9 (p<0.01 vs. vehicle). The most pronounced effect was observed for treatment with SM1 KM03702. The beneficial effect was already observed on day 19 post immunization (EAE clinical score of 0.5±0.2 vs. 1.1±0.3 in vehicle group). This effect increased until day 27, when the clinical score reached 0.3±0.3.

SM7-RF02433 and SM9-KM01484 also ameliorated EAE starting from day 21 post immunization (EAE clinical score of 0.6±0.1 and 0.8±0.3 in SM7- and SM9-treated groups, respectively, vs. 1.1±0.3 in vehicle group). Apparently, SM6 did not show any beneficial effect in this experiment, nonetheless it was also chosen for further analysis in the next experiment in order to provide some comparative results.

Figure 4:
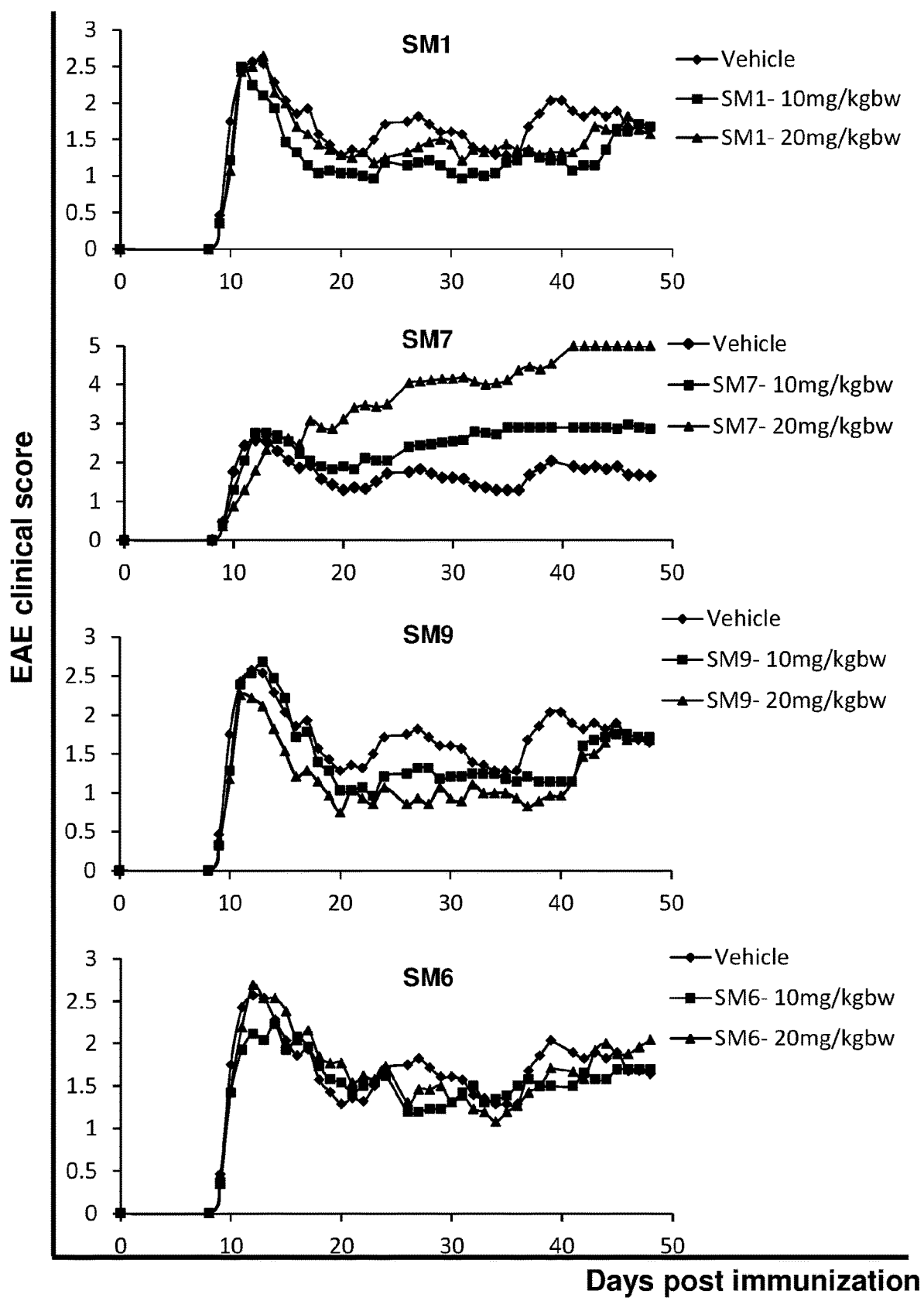
FIG. 4—The effect of SM1, SM6, SM7 and SM9 in RR-EAE. EAE clinical score in RR-EAE mice, each group (n=14) treated with SM1, SM7, SM9 or SM6 at two dosages, 10 mg/kg/day (squares) and 20 mg/kg/day (triangles), as compared with vehicle alone (5% DMSO in PBS, 200 µl/mouse) (diamonds) from day 9 for 30 days.

Experiments were repeated with the 4 above-mentioned molecules SM1, SM6, SM7 & SM9. The experiment was conducted under similar conditions as the previous one, except that two dosages of the molecules were administered: a dose of 10 mg/kg and dose of 20 mg/kg, namely 250 g/mouse and 500 g/mouse on days 9-38 (see FIG. 4).

A significant beneficial effect was observed for treatment with the low dosage of 10 mg/kg of SM1 (p=0.0005 vs. vehicle). A trend for amelioration was also observed for the high dose of SM1, though it was not statistically significant (p=0.09). Moreover, treatment with both the low and the high dosage of SM9 ameliorated EAE. Here, the high dosage of 20 mg/kg was more potent compared to the low dosage (p=0.049 for 10 mg/kgbw and p=0.0001 for 20 mg/kg). Similar to the previous experiment, the amelioration was primarily observed during the second and the third relapses (on days 23-31 and on days 37-44, respectively).

The effect of treatment with SM6 was milder and not significant. However, contrary to the previous experiment, it was observed that SM7 has a toxic effect that results in death of most of the treated mice: by the end of the experiment (day 48), 8 mice died in the low dose group of 10 mg/kg and all of the mice died in the high dose group of 20 mg/kg.

Figure 5:
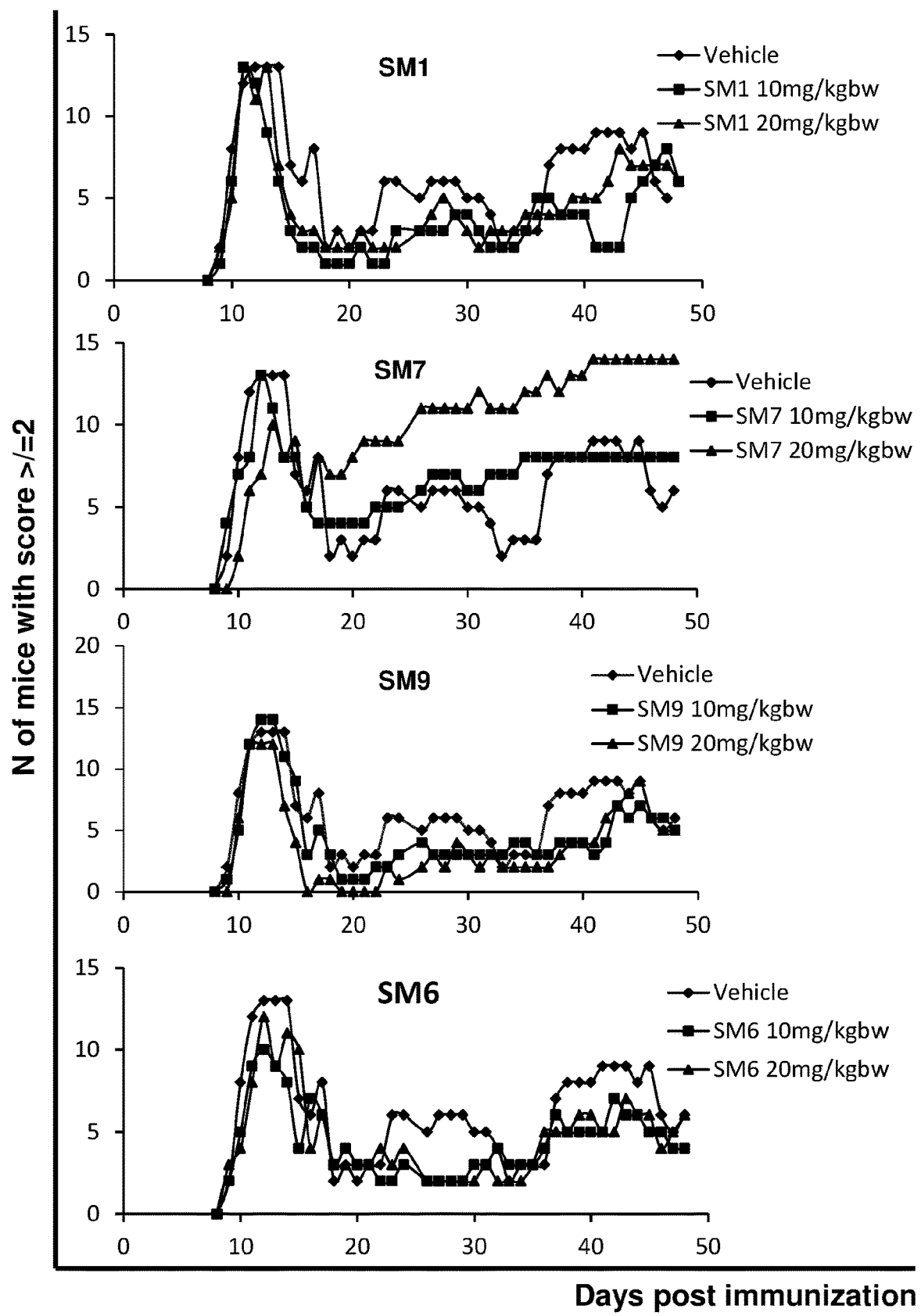
FIG. 5—The effect of SM1, SM6, SM7 and SM9 on the number of mice with moderate-severe EAE. The number of mice with clinical score above or equal 2, per day, per group (10 mg/kg/day—squares, 20 mg/kg/day—triangles, vehicle—diamonds).

The number of animals exhibiting at least a score of 2 (hind limbs paresis) at any time during the study was also analyzed (see FIG. 5). As shown, similarly to the average clinical score analysis, both SM1 (primarily the low dosage of 10 mg/kg) and SM9 (primarily the high dosage of 20 mg/kg) demonstrated a beneficial effect in the context of reduced number of mice with moderate-severe EAE scores.

Interestingly, in the group of mice treated with SM6 the number of mice with a more severe EAE was reduced (during the second relapse: 2-3 mice in SM6-treated groups vs. 5-6 mice in vehicle group, and during the third relapse: 5-7 in SM6-treated groups vs. 8-9 mice in vehicle group). Apparently, SM6 has an effect on the amelioration of severe EAE.

Example 3

Effect of SM1, SM6, SM7 and SM9 on Demyelination in EAE

Figure 6A:
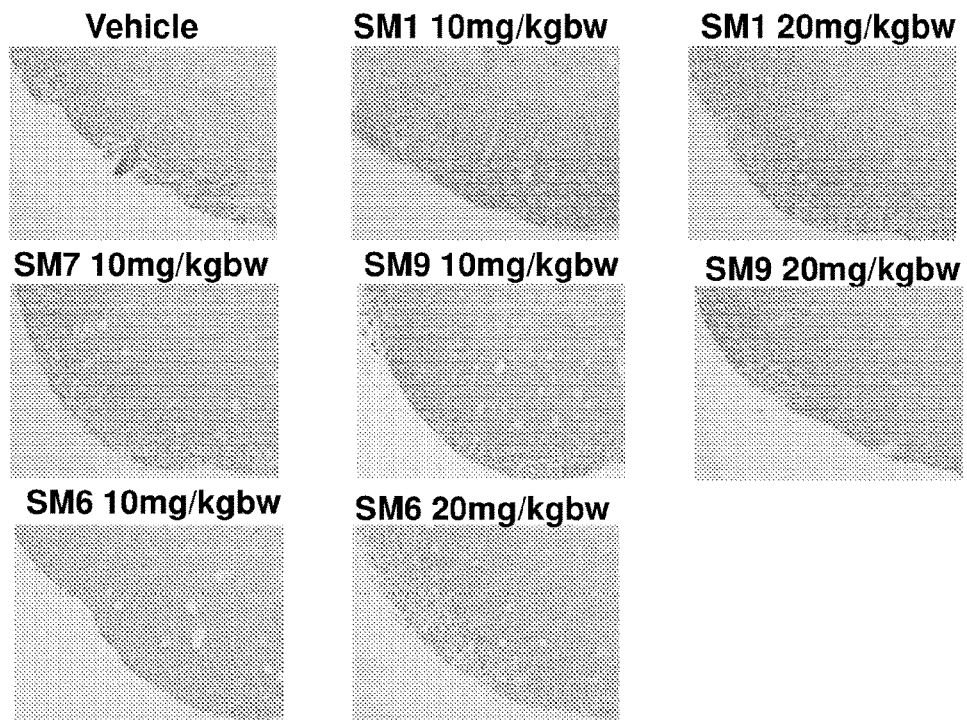
FIG. 6—The effect of SM1, SM6, SM7 and SM9 on demyelination. (A) Representative images of the lumbar spinal cord section, stained with LFB (anterio lateral funiculus), of mice treated with vehicle, SM1 10 mg/kg/day, SM1 20 mg/kg/day, SM7 10 mg/kg/day, SM9 10 mg/kg/day, SM9 20 mg/kg/day, SM6 10 mg/kg/day and SM6 20 mg/kg/day. (B) Quantification of myelinated area. The graph shows percent (%) LFB-stained area out of the total spinal cord section, at day 48 post immunization. Quantification was performed using Image J software on 6 mice/group and 3 sections/mouse.
Figure 6B:
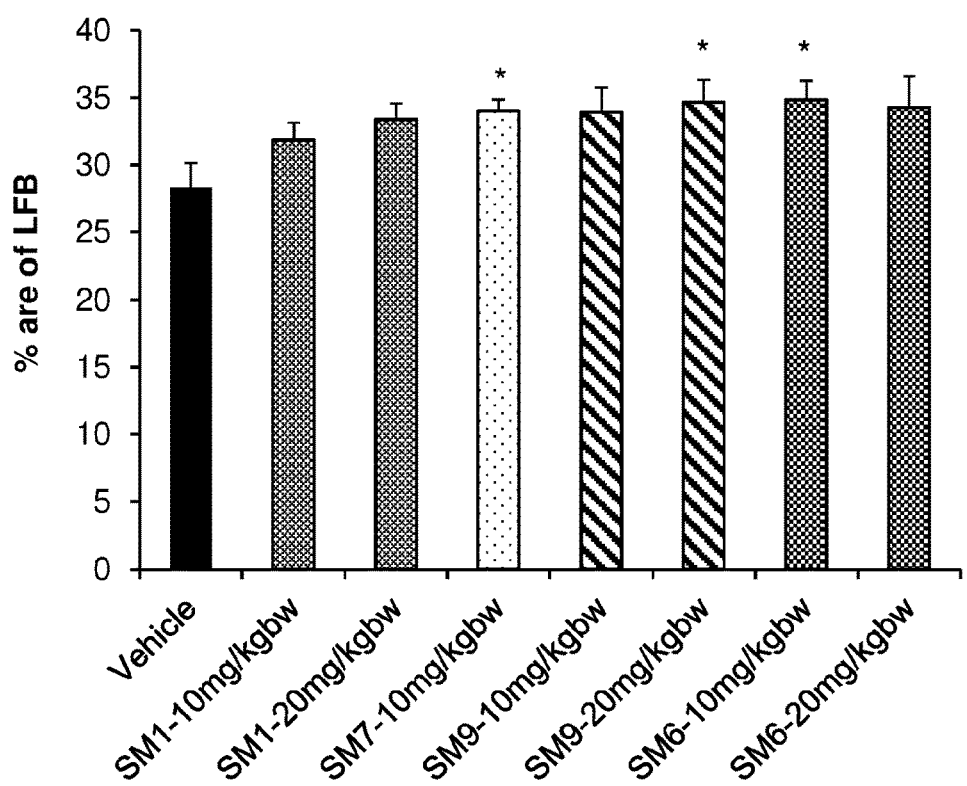

The direct effect of the SMs on the demyelination and remyelination processes was analyzed. Spinal cord was removed from 6 mice of each group and the lumbar segment of the spinal cord was sectioned (10 m coronal paraffin section) and was processed for LFB-H&E (luxol fast blue with H&E) for myelin and infiltrates staining. As shown in FIG. 6A, an increased number of infiltrates as well as demyelination was observed in vehicle-treated group. There was a slight trend for elevation in % myelinated area for all examined SMs (FIG. 6B), though a significant effect was observed for 10 mg/kg SM7 (34.0±0.8% in 10 mg/kg SM7-treated group vs. 28.3±1.8% in vehicle p=0.04, the high dosage was not examined due to toxicity), as well as for 20 mg/kg SM9 (34.6±1.6%, p=0.03), and 10 mg/kg SM6 (34.8±1.6%=p, 0.03). These results may indicate increased remyelination processes or decreased demyelination in response to these SMs treatment, or both.

Example 4

The Effect of SM1, SM7 and SM9 on Neurogenesis In Vitro

Next, the effect of the small molecules on neurogenesis in a P19 differentiation model was measured. It has been demonstrated that P19 cells, murine embryo-derived teratocarcinoma cells, differentiate into neurons in response to retinoic acid (RA) stimulation and that this differentiation can be blocked by addition of rhBMP-2 (bone morphogenetic protein-2) [8]. Neuronal differentiation is marked by the expression of the neuronal marker MAP-2, while the addition of BMP-2 reduces the levels of this marker. Addition of the murine anti-BMP-2/4 monoclonal antibody reverses the effect of BMP-2 and induces acquisition of neuronal phenotype. Thus, the effect of SM1, SM7 and SM9 on the expression of the neuronal marker MAP-2 in P19 cells was examined in the presence of RA and BMP-2. Three concentrations of the molecules were tested: 0.625 μM, 1.25 μM and 2.5 μM.

Figure 7A:
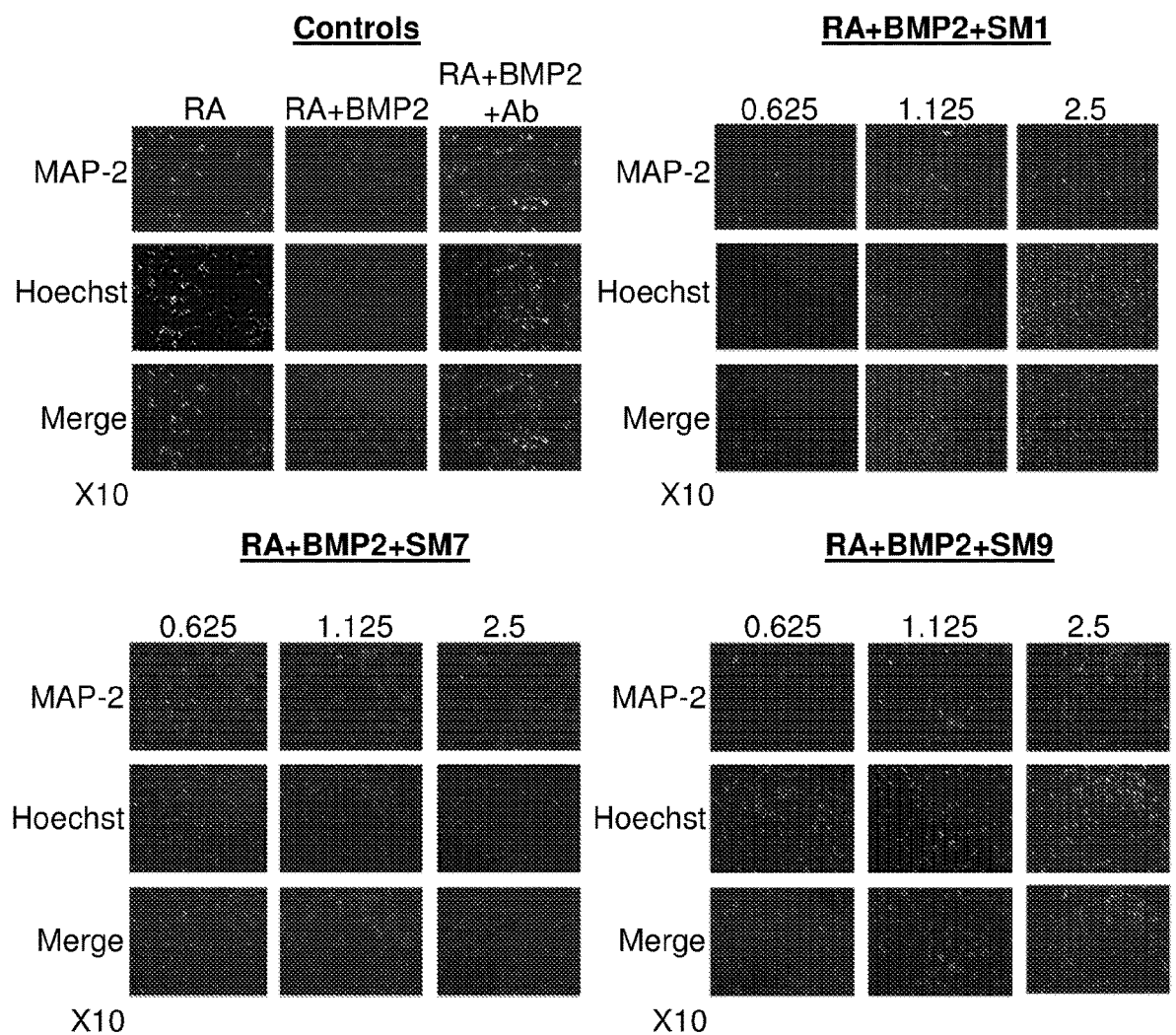
FIG. 7—The effect of SM1, SM7 and SM9 on neuronal phenotype in P19 cells. (A) Representative images of P19 cells on day 8, stained with MAP-2 and Hoechst. Images were obtained using Olympus BX 81 inverted fluorescent microscope. (B) Analysis of % MAP-2 positive cells. Analysis was performed by Image J software.
Figure 7B:
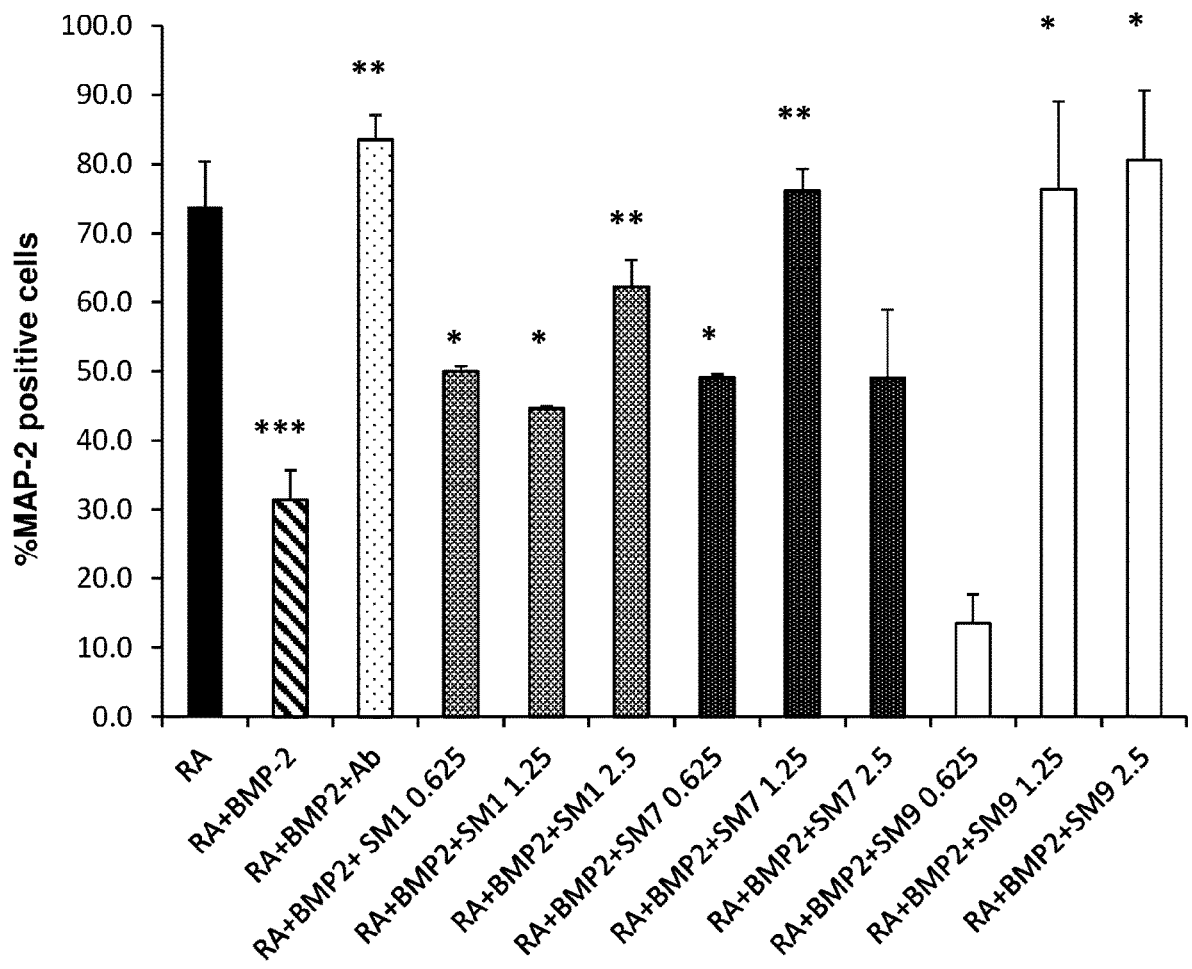

No MAP-2 positive cells were observed in absence of any stimulation. As demonstrated in FIGS. 7A-7B, RA stimulation of P19 cells increased the number of MAP-2$^+$ cells (73.8±6.5%). Addition of rhBMP-2, significantly reduced the number of MAP-2$^+$ cells (31.4±4.3%), i.e. blocked neuronal phenotype, whereas addition of the anti-BMP-2/4 mAb reversed the effect of BMP-2 by increasing the number of MAP-2$^+$ cells (83.6±3.5%, p<0.01 vs. RA+BMP-2). Similar to the effect of the anti-BMP-2/4 neutralizing mAb, SM1, SM7 and SM9 reversed the effect of BMP-2, and increased the number of MAP-2$^+$cells (neurons), compared to merely RA+BMP-2 stimulation.

SM1 induced neuronal phenotype at all examined concentrations, but most notably at the higher concentration of 2.5 μM (62.2±3.9%, p<0.01 vs. RA+BMP-2).

A dose-dependent effect was also observed for SM7, which induced neuronal phenotype at both the low and the mild concentrations, particularly at the mild concentration of 1.25 μM (76.1±3.1%, p<0.01 vs. RA+BMP-2). No significant effect was observed for the higher concentration, perhaps because of a toxic effect. SM9 was not effective at the low concentration and induced neurogenesis in both the mild and the higher concentrations of 1.25 M and 2.5 M (76.4±12.6% and 80.6±10.0% respectively, p<0.05 vs. RA+BMP-2).

Example 5

The Effect of SM1, SM7 and SM9 on SMAD Signaling in P19 Cells

The canonical BMP signal is known to be mediated via SMAD phosphorylation. BMPs transduce signals by binding to complexes of type I and II serine/threonine kinase receptors. Ligand binding induces phosphorylation of the receptors, which then activate canonical signaling via receptor Smads (R-Smads) 1, 5 and 8. R-Smads are phosphorylated by the activated type I receptor. They then complex with Smad4, triggering nuclear translocation [16]. The effect of the SMs on the phosphorylation of the canonical SMAD1/5/8 signaling, induced in P19 cells in response to stimulation with BMP-2, was examined.

Figure 8A:
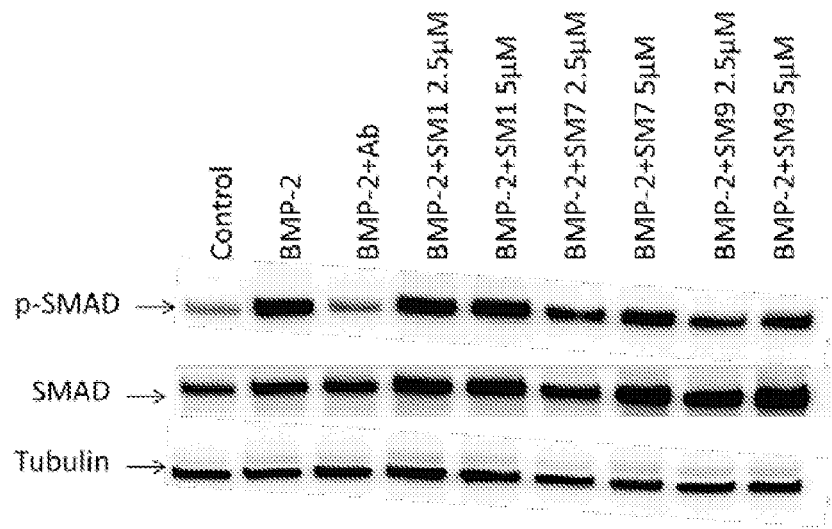
FIG. 8—The effect of SM1, SM7 and SM9 on SMAD1/5/8 signaling, detected by WESTERN blot. (A) Western blot of phosphorylated SMAD (p-SMAD), total SMAD, and tubulin in response to no stimulation ("Control") or stimulation with BMP-2, BMP-2+ anti-BMP-2/4 Ab, BMP-2+ SM1 or SM7 or SM9 at 2.5 µM and 5 µM as indicated. (B) Quantification of p-SMAD/tubulin as performed by Image J software.
Figure 8B:
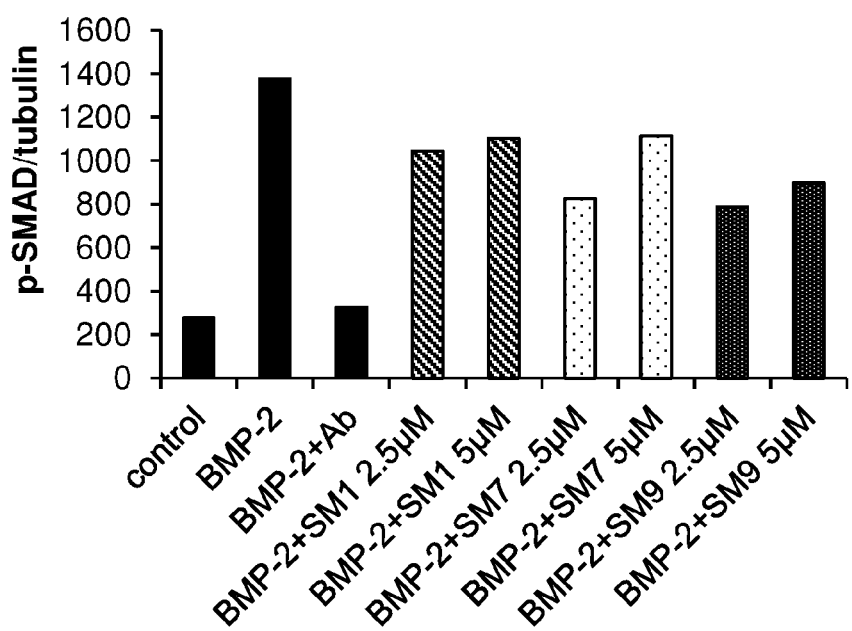

As demonstrated in FIGS. 8A and 8B, stimulation of P19 cells with rhBMP-2 for 4 hours, induced p-SMAD expression (normalized to tubulin expression) by 4.9-fold. Addition of anti-BMP-2/4 mAb inhibited p-SMAD expression by 76.2% compared to stimulation with BMP-2 alone. SM7 and SM9, particularly at the lower concentration of 2.5 μM, had the most pronounced effect on SMAD phosphorylation (reduction by 40.0% and 42.7% in p-SMAD/tubulin for SM7 and SM9, respectively, compared to stimulation with merely BMP-2). SM1 had only a mild effect on SMAD phosphorylation (inhibition of 24.2% and 19.9% for 2.5 μM and 5 μM, respectively).

Example 6

The Effect of SM1, SM7, SM9 and SM6 on BMP-4 Inhibition

Due to the high homology between BMP-2 and BMP-4, the ability of the SMs to inhibit BMP-2 and BMP-4 signaling (similar to the effect of the anti-BMP-2/4 mAb) was also examined. BMP-4 neutralization was analyzed using the same bioassay that was used for screening (namely, ATDC5 bioassay with ALP and viability detection), except that for stimulation of ATDC5 cells rhBMP-4 was employed instead of rhBMP-2.

Figure 9:
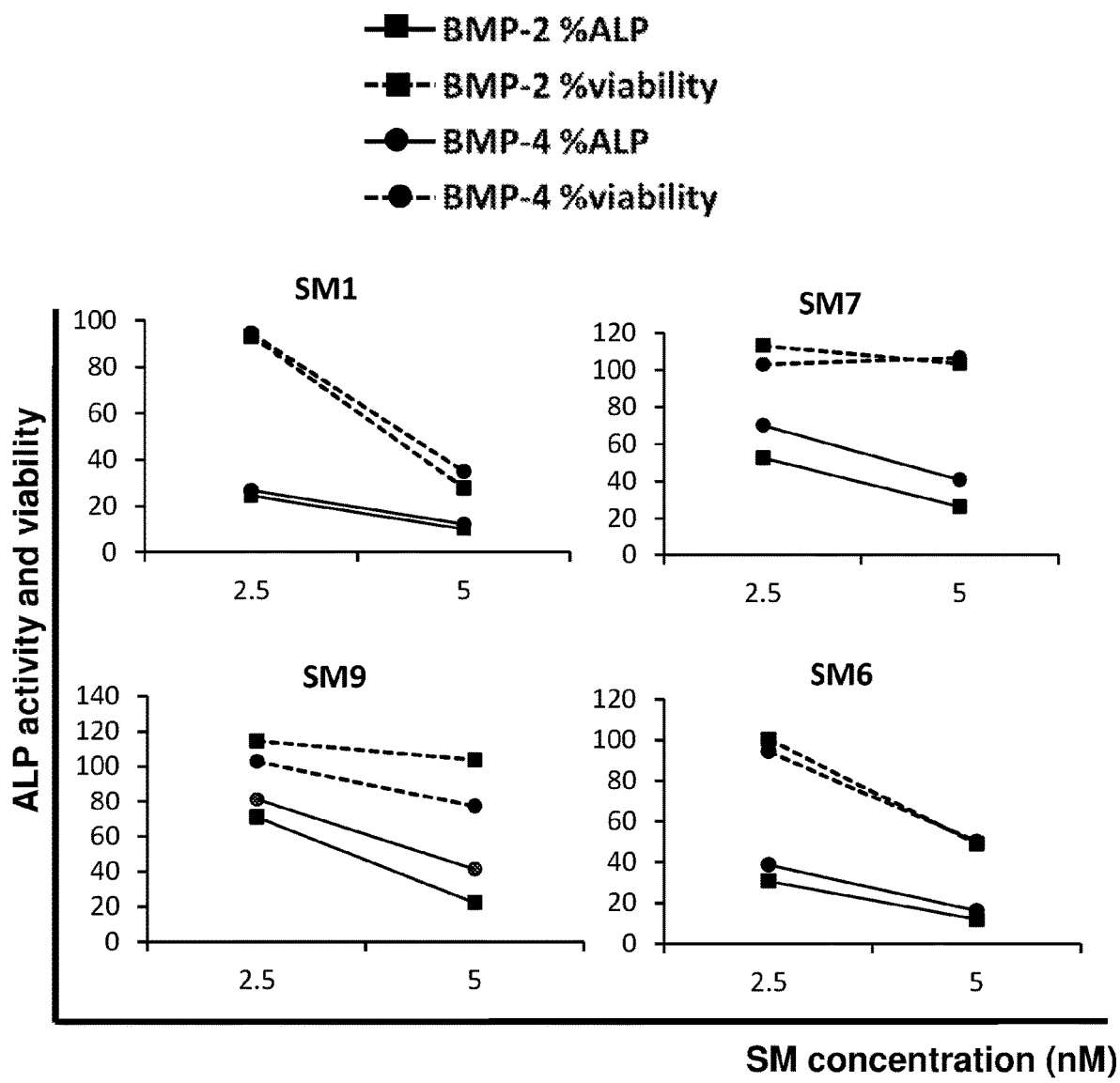
FIG. 9—The effect of SM1, SM7, SM9 and SM6 in an ATDC5 bioassay induced by BMP-4/BMP-2. Percentage of ALP induction and percentage of cell viability for SM1, SM7, SM9 and SM6 at 2.5 µM and 5 µM in the presence of BMP-4 stimulation vs. BMP-2 stimulation.

As shown in FIG. 9, SM1 and SM6 had the same effect on ALP production induced by BMP-4 and by BMP-2. Both SM7 and SM9 seemed to inhibit BMP-2 slightly more than BMP-4 (for 2.5 μM SM7-47.3% inhibition of BMP-2, compared to 29.8% inhibition of BMP-4, and for 2.5 μM SM9-29.1% inhibition of BMP-2, compared to 18.9% inhibition of BMP-4).

Example 7

The Effect of SM1, SM7, SM9 and SM6 on De Novo Expression of the Neuroblasts Marker Doublecortin (DCX) in the Subventricular Zone (SVZ) and the Subgranular Zone (SGZ)

Figure 10A:
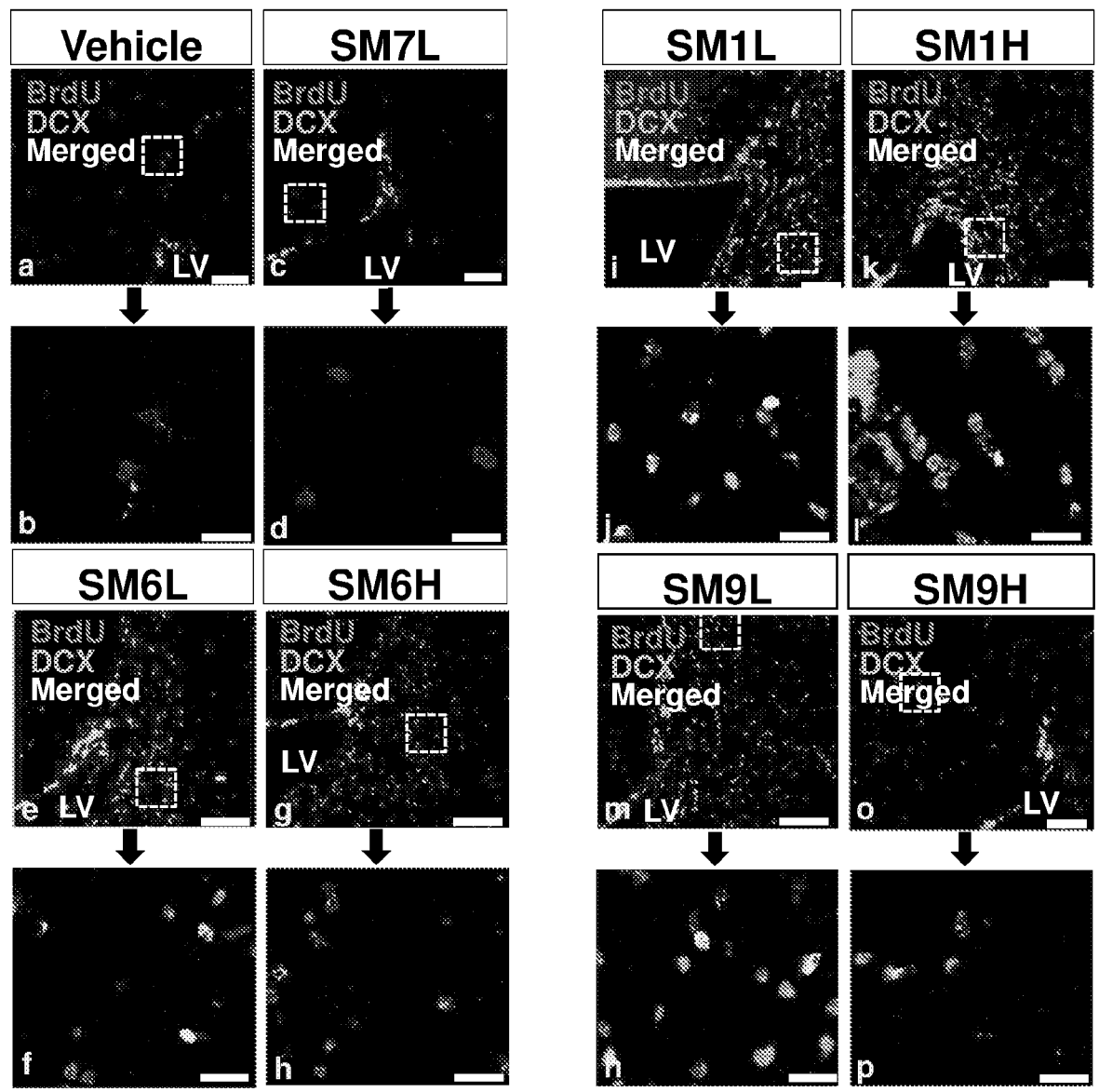
FIG. 10—The effect of SM1, SM7, SM9 and SM6 on de novo expression of neuroblasts marker doublecortin in the SVZ. (A) Immunofluorescence images showing the labeling of BrdU and doublecortin (DCX) in the SVZ. Images were obtained using Zeiss 710 confocal microscope, coronal sections. LV, lateral ventricle, SVZ, subventricular zone. Scale bar for images: a, c, e, g, i, k, m, o=100 µm (magnification ×10), and images: b, d, f, h, j, l, n, p=20 µm (magnification ×63). (B) Quantification of BrdU$^+$ DCX$^+$ cells in the SVZ. Analysis was performed using image J software on 3 sections from each mouse (3 mice from each group, total n=9). Values are given as mean±SEM and the results of Student's t-test are represented as *p<0.05.
Figure 10B:
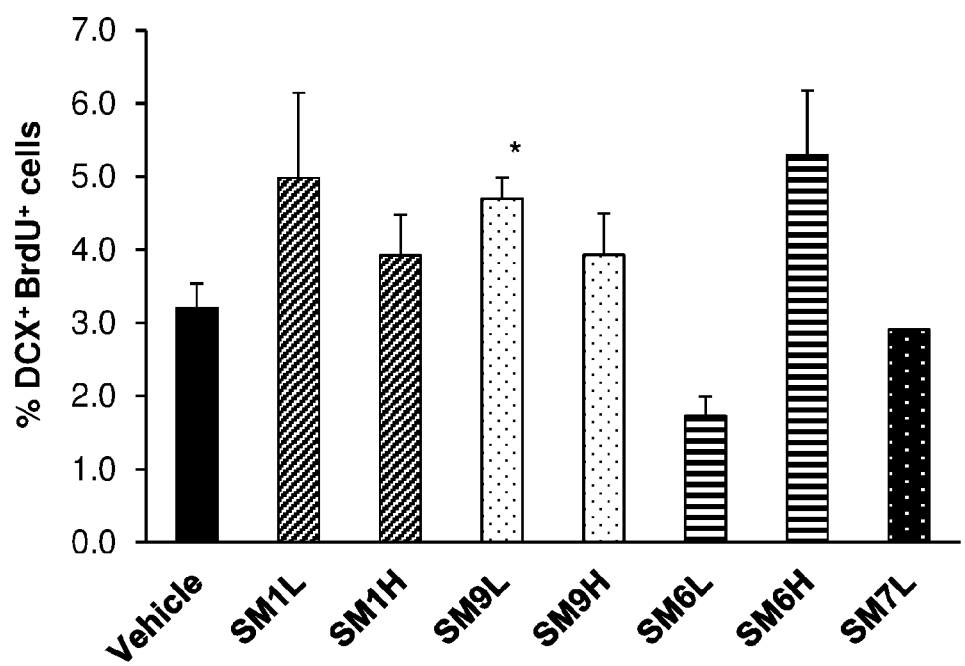

RR-EAE induced mice were intraperitoneally injected with 250 μg/mouse (Low-L) or 500 μg/mouse (High-H) of the small molecules SM1, SM7, SM9, SM6, or the corresponding vehicle. The SMs were injected each day starting on day 9 post immunization for 30 days. For immunohistochemical analysis, 3 mice of each group were intraperitoneally injected daily with bromo-2'-deoxyuridine (BrdU) starting from day 9 post immunization for 8 following days. As can be seen in FIGS. 10A-10B quantification of BrdU$^+$ DCX$^+$ cells in the SVZ of the mice with EAE revealed that SM9L (the low dose of SM9) caused a significant increase in BrdU$^+$ DCX$^+$ cells. The results also reveal a trend for increased induction of BrdU$^+$ DCX$^+$ cells by SM9H, SM1L, SM1H and SM6H as compared to the control vehicle.

Figure 11A:
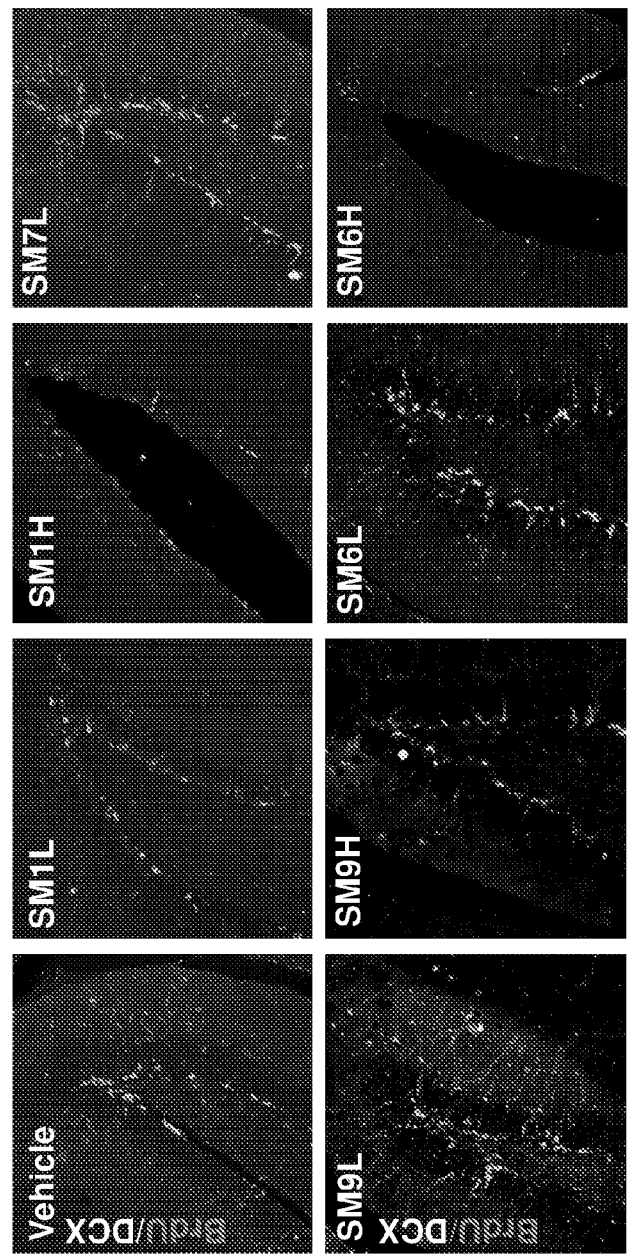
FIG. 11—The effect of SM1, SM7, SM9 and SM6 on de novo expression of doublecortin in the SGZ. (A) are immunohistochemical images showing the labeling of BrdU⁺ DCX⁺ cells in the SGZ. Images were obtained using Olympus 8.1 microscope (magnification ×10). (B) Quantification of BrdU⁺DCX⁺ cells in the SGZ. Analysis was performed using image J software on 3 sections from each mouse (3 mice from each group, total n=9). Values are given as mean±SEM and the results of Student's t-test are represented as *p<0.05.
Figure 11B:
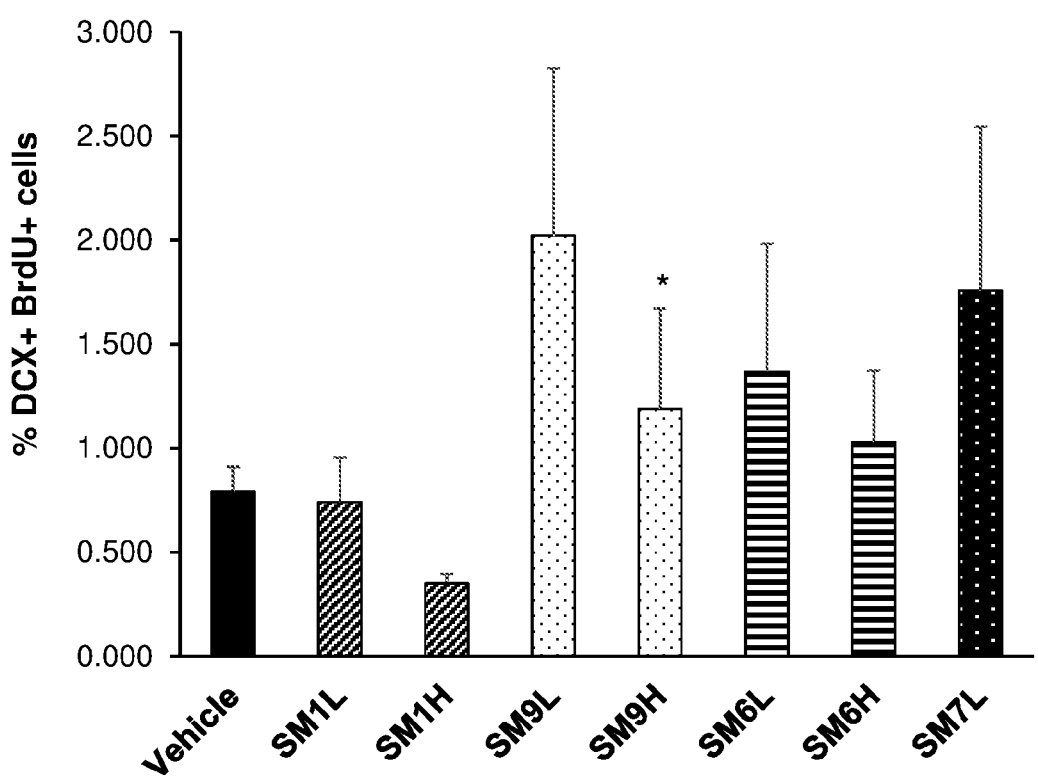

Next, the amount of BrdU$^+$ DCX$^+$ cells in the SGZ of mice was evaluated. FIGS. 11A-11B show immunohistochemical labeling of BrdU$^+$ DCX$^+$ cells in mice with EAE after treatment with the SMs or with vehicle. Quantification of the BrdU$^+$ DCX$^+$ cells revealed a significant increased induction in BrdU$^+$ DCX$^+$ cells in the SGZ by SM9H along with a trend for increased BrdU$^+$ DCX$^+$ cells induction by SM9L, SM6L and SM7L as compared to treatment with the vehicle.

Example 8

The Effect of SM1, SM7, SM9 and SM6 on De Novo Expression of Mature Neurons Marker NeuN in the SGZ.

Figure 12A:
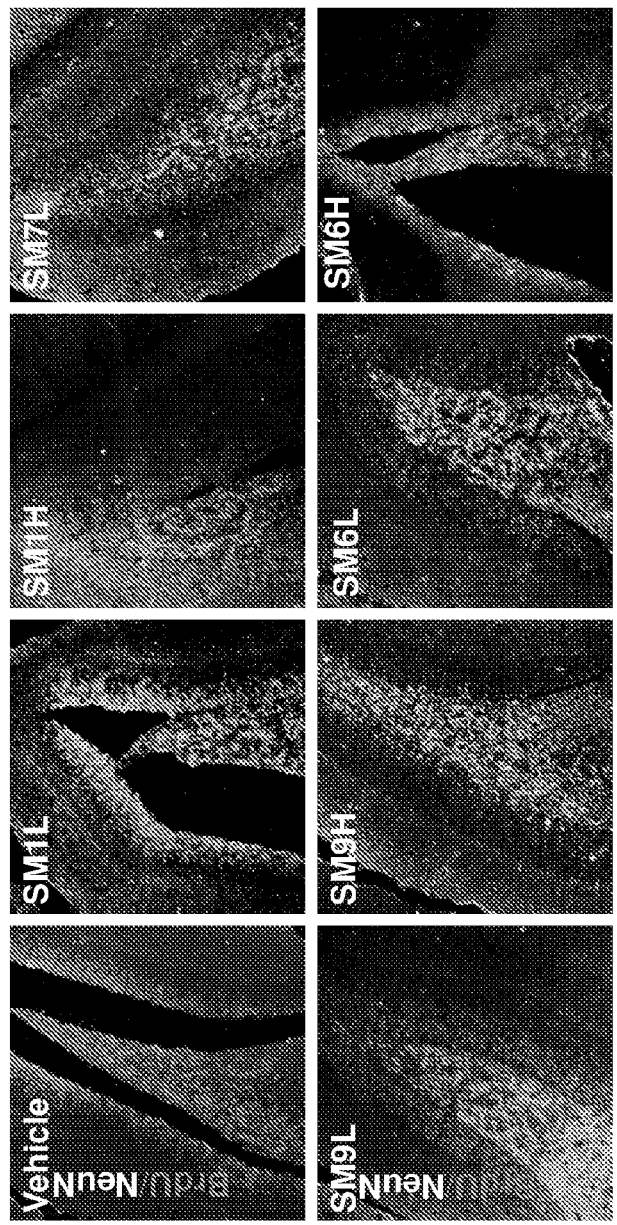
FIG. 12—The effect of SM1, SM7, SM9 and SM6 on de novo expression of mature neurons marker NeuN in the SGZ. (A) immunohistochemical images showing the labeling of BrdU⁺NeuN⁺ cells in the SGZ. Images were obtained using Olympus 8.1 microscope (magnification ×10). (B) Quantification of BrdU⁺ Neu⁺ in the SGZ. Analysis was performed using image J software on 3 sections from each mouse (3 mice from each group, total n=9). Values are given as mean±SEM and the results of Student's t-test are represented as *p<0.05.
Figure 12B:
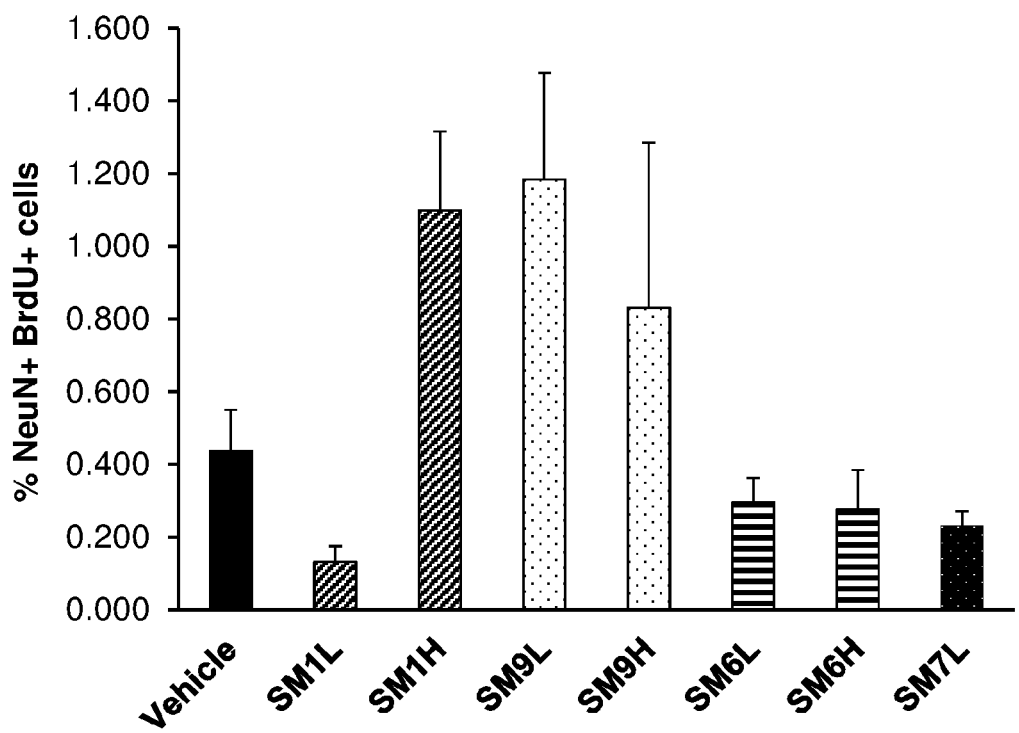

In this experiment, the amount of BrdU+NeuN+ cells in the SGZ of mice was evaluated. FIGS. 12A-12B show immunohistochemical labeling of BrdU+NeuN+ cells in mice with EAE that were treated with SMs or vehicle, using Olympus 8.1 microscope (magnification ×10). Quantification of BrdU+NeuN+ cells revealed a significant increased induction in BrdU+NeuN+ cells in the SGZ by SM1H and SM9L treated mice along with a trend for increased BrdU+NeuN+ cells induction by SM9H, as compared to the treatment with the vehicle.

REFERENCES CITED

References considered to be relevant as background to the presently disclosed subject matter are listed below:
[1] Trapp, B. D. and Nave, K. A. *Annu. Rev. Neurosci.* 2008; 31:247-269.
[2] Grinspan J. B. (2015) *Vitamins and Hormones*, Chapter 6, volume 99, pages 195-222.
[3] US 2015/139983
[4] US 2008/0249038
[5] Simonini M. V. et al. *ASN Neuro.* 2010 Jan. 15; 2(1); e00025
[6] Li D. et al. *Hippocampus* 2008; 18: 692-8
[7] Mabie P. C. et al. *J. Neurosci.* 1997, 17: 4112-4120
[8] Gross R. E. et al. *Neuron* 1996, 17: 595-606
[9] Gomes W. A. et al. *Dev. Biol.* 2003, 255: 164-177
[10] Lim D. A. et al. *Neuron* 2000, 28: 713-726
[11] WO 11/019678
[12] US 2006217390
[13] WO 03/105857
[14] US 2004039037
[15] Kurtzke, J. F. neurology 1983: 33(11): 1444-1452
[16] Bani-Yaghoub M, Felker J M, Sans C, Naus C C. Exp Neurol. 2000; 162:13-26.
[17] WO 2013/186777

Acknowledgement of the above references herein is not to be inferred as meaning that these are in any way relevant to the patentability of the presently disclosed subject matter.

The invention claimed is:

1. A method of treating multiple sclerosis (MS) in a subject, the method comprising the step of administering to the subject a therapeutically effective amount of a compound having the general Formula (I) or a salt thereof:

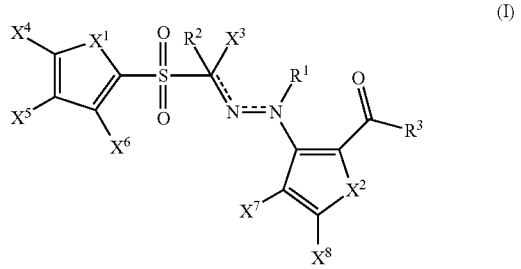

(I)

wherein
$X^1$ and $X^2$ are each independently S, O or N—$R^4$, wherein $R^4$ is selected from the group consisting of H, alkyl, cycloalkyl, aryl and heteroaryl;
$X^3$ is selected from the group consisting of CN, halogen, $NO_2$, CO—$X^9$ and $SO_2X^9$, wherein $X^9$ is selected from the group consisting of OH, O⁻ and $NH_2$;
$X^4$, $X^5$, $X^6$, $X^7$, and $X^8$ are each independently selected from the group consisting of H, alkyl, cycloalkyl, aryl, amine, halogen, alkoxy, hydroxy, heteroaryl, $NO_2$, CN, CO—$X^{10}$ and $SO_2X^{10}$, wherein $X^{10}$ is selected from the group consisting of OH, O⁻ and $NH_2$;
one of $R^1$ and $R^2$ is absent and the other $R^1$ and $R^2$ is selected from the group consisting of H, alkyl, cycloalkyl, aryl, amine, halogen, alkoxy, heteroaryl, CN, CO-$X^{11}$ and $SO_2X^{11}$, wherein $X^{11}$ is selected from the group consisting of OH, O⁻ and $NH_2$;
$R^3$ is selected from the group consisting of $OR^5$, O⁻ and $NR^6R^7$, wherein $R^5$, $R^6$, and $R^7$ are each independently selected from the group consisting of H, alkyl, cycloalkyl and aryl; and
wherein each of the dotted lines independently represents a single or a double bond.

2. The method of claim 1, wherein the compound has the Formula (Ia) or a salt thereof:

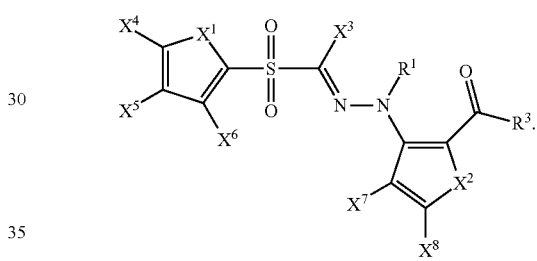

3. The method of claim 2, wherein each one of $X^1$ and $X^2$ is S.

4. The method of claim 2, wherein $X^3$ is CN.

5. The method of claim 2, wherein each one of $X^4$, $X^5$, $X^6$, $X^7$, and $X^8$ is H.

6. The method of claim 2, wherein $R^1$ is H.

7. The method of claim 2, wherein $R^3$ is $OR^5$, wherein $R^5$ is methyl or ethyl.

8. The method of claim 2, wherein the compound is SM1:

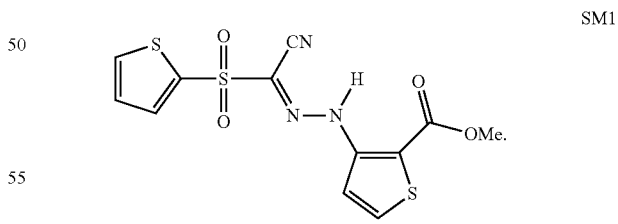

SM1

9. The method of claim 2, wherein the multiple sclerosis is relapsing remitting multiple sclerosis.

10. The method of claim 2, further comprising the step of administering an additional therapeutic agent to said subject.

\* \* \* \* \*